US012678276B2

(12) United States Patent
Barnett

(10) Patent No.: US 12,678,276 B2
(45) Date of Patent: Jul. 14, 2026

(54) EXCHANGEABLE OPTICS AND THERAPEUTICS USING MAGNETIC TACKS

(71) Applicant: California LASIK & Eye, Inc., Sacramento, CA (US)

(72) Inventor: Bradley P. Barnett, Sacramento, CA (US)

(73) Assignee: California LASIK & Eye, Inc., Sacramento, CA (US)

( * ) Notice: Subject to any disclaimer, the term of this patent is extended or adjusted under 35 U.S.C. 154(b) by 302 days.

(21) Appl. No.: 18/633,919

(22) Filed: Apr. 12, 2024

(65) Prior Publication Data

US 2024/0252310 A1    Aug. 1, 2024

Related U.S. Application Data

(63) Continuation-in-part of application No. 17/839,407, filed on Jun. 13, 2022, now Pat. No. 11,974,911,
(Continued)

(51) Int. Cl.
*A61F 9/007* (2006.01)
*A61F 2/16* (2006.01)
(Continued)

(52) U.S. Cl.
CPC .......... *A61F 2/1648* (2013.01); *A61F 2/1624* (2013.01); *A61B 2017/044* (2013.01);
(Continued)

(58) Field of Classification Search
CPC ............ A61F 2/1648; A61F 2002/1681; A61F 2002/16902; A61F 2210/009; A61F 2220/0008
See application file for complete search history.

(56) References Cited

U.S. PATENT DOCUMENTS

| | | | |
|---|---|---|---|
| 3,937,222 | A | 2/1976 | Banko |
| 4,035,007 | A | 7/1977 | Harrison et al. |

(Continued)

FOREIGN PATENT DOCUMENTS

| | | | |
|---|---|---|---|
| AU | 2018271403 B2 | 2/2019 | |
| AU | 2017345731 B2 | 10/2019 | |

(Continued)

OTHER PUBLICATIONS

Reinstein, D. Z.; Vida, R. S.; Archer, T. J. Visual Outcomes, Footplate Position and Vault Achieved with the Visian Implantable Collamer Lens for Myopic Astigmatism. Clin Ophthalmol 2021, 15, 4485-4497. DOI: 10.2147/OPTH.S330879 From NLM PubMed-not-Medline.

(Continued)

*Primary Examiner* — Javier G Blanco
(74) *Attorney, Agent, or Firm* — Mark P. Mathison

(57) ABSTRACT

An exchangeable optics system includes magnetic fixation points that are anchored to the outside of the eye. The fixation points can include magnetic barbed tacks, magnetic soft tissue screws, or a sclera buckle with permanent magnets. Fiducials on the fixation points help with visibility during implantation of an exchangeable intraocular lens (IOL) or other devices. The exchangeable optic can be suspended within the eye by way of tethers having ends of magnetic metal or permanent magnetic material that magnetically couple with the magnetic fixation points. The lengths of the suspension tethers can be adjusted in small increments with other magnets in order to place the lens into position with a proper three-dimensional orientation within the eye.

11 Claims, 26 Drawing Sheets

Related U.S. Application Data which is a continuation of application No. 17/471,496, filed on Sep. 10, 2021, now Pat. No. 11,357,620.

(51) Int. Cl.

| | |
|---|---|
| A61B 17/04 | (2006.01) |
| A61B 17/064 | (2006.01) |
| A61L 27/54 | (2006.01) |

(52) U.S. Cl.
CPC ..... *A61B 2017/0648* (2013.01); *A61F 2/1602* (2013.01); *A61F 2002/1682* (2015.04); *A61F 2002/16902* (2015.04); *A61F 9/00781* (2013.01); *A61L 27/54* (2013.01)

(56) References Cited

U.S. PATENT DOCUMENTS

| | | | |
|---|---|---|---|
| 4,144,057 A | | 3/1979 | Melton et al. |
| 4,168,547 A | | 9/1979 | Konstantinov et al. |
| 4,298,996 A | * | 11/1981 | Barnet ..................... A61F 2/16 |
| | | | 623/6.43 |
| 4,337,090 A | | 6/1982 | Harrison |
| 4,409,691 A | | 10/1983 | Levy |
| 4,435,856 A | | 3/1984 | L'Esperance |
| 4,494,254 A | | 1/1985 | Lopez |
| 4,502,159 A | | 3/1985 | Woodroof et al. |
| 4,505,767 A | | 3/1985 | Quin |
| 4,601,722 A | | 7/1986 | Kelman |
| 4,681,102 A | | 7/1987 | Bartell |
| 4,693,245 A | | 9/1987 | Pao |
| 4,741,330 A | | 5/1988 | Hayhurst |
| 4,769,035 A | | 9/1988 | Kelman |
| 4,816,031 A | | 3/1989 | Pfoff |
| 4,828,558 A | | 5/1989 | Kelman |
| 4,830,262 A | | 5/1989 | Ishibe |
| 4,842,601 A | | 6/1989 | Smith |
| 4,878,910 A | | 11/1989 | Koziol et al. |
| 4,894,100 A | | 1/1990 | Yamauchi et al. |
| 4,932,971 A | | 6/1990 | Kelman |
| 4,950,272 A | | 8/1990 | Smirmaul |
| 4,950,289 A | | 8/1990 | Krasner |
| 4,960,418 A | | 10/1990 | Tennant |
| 5,026,396 A | | 6/1991 | Darin |
| 5,098,444 A | | 3/1992 | Feaster |
| 5,114,504 A | | 5/1992 | AbuJudom, II et al. |
| 5,123,905 A | | 6/1992 | Kelman |
| 5,133,747 A | | 7/1992 | Feaster |
| 5,147,369 A | | 9/1992 | Wagner |
| 5,152,788 A | | 10/1992 | Isaacson et al. |
| 5,201,762 A | | 4/1993 | Hauber |
| 5,222,981 A | | 6/1993 | Werblin |
| 5,304,182 A | | 4/1994 | Rheinish et al. |
| 5,323,788 A | | 6/1994 | Silvestrini et al. |
| 5,354,335 A | | 10/1994 | Lipshitz et al. |
| 5,358,520 A | | 10/1994 | Patel |
| 5,378,475 A | | 1/1995 | Smith et al. |
| 5,410,375 A | | 4/1995 | Fiala |
| 5,417,369 A | | 5/1995 | Lipson |
| 5,466,233 A | | 11/1995 | Weiner et al. |
| 5,507,805 A | | 4/1996 | Koeniger |
| 5,578,081 A | | 11/1996 | McDonald |
| 5,593,437 A | | 1/1997 | Arita et al. |
| 5,616,120 A | | 4/1997 | Andrew et al. |
| 5,628,795 A | | 5/1997 | Langerman |
| 5,641,364 A | | 6/1997 | Golberg et al. |
| 5,711,969 A | | 1/1998 | Patel et al. |
| 5,728,155 A | | 3/1998 | Anello et al. |
| 5,735,892 A | | 4/1998 | Myers et al. |
| 5,764,511 A | | 6/1998 | Henderson et al. |
| 5,769,890 A | | 6/1998 | McDonald |
| 5,814,103 A | | 9/1998 | Lipshitz et al. |
| 5,824,074 A | | 10/1998 | Koch |
| 5,860,985 A | | 1/1999 | Anschutz |
| 5,876,442 A | | 3/1999 | Lipshitz et al. |
| 5,885,619 A | | 3/1999 | Patel et al. |
| 5,895,422 A | | 4/1999 | Hauber |
| 5,902,598 A | | 5/1999 | Chen et al. |
| 5,928,283 A | | 7/1999 | Gross et al. |
| 5,944,725 A | | 8/1999 | Cicenas et al. |
| 5,955,110 A | | 9/1999 | Patel et al. |
| 5,968,094 A | | 10/1999 | Werblin et al. |
| 5,968,096 A | | 10/1999 | Whitson et al. |
| 6,027,531 A | | 2/2000 | Tassignon |
| 6,066,171 A | | 5/2000 | Lipshitz et al. |
| 6,090,141 A | | 7/2000 | Lindstrom |
| 6,113,633 A | | 9/2000 | Portney |
| 6,197,057 B1 | | 3/2001 | Peyman et al. |
| 6,197,058 B1 | | 3/2001 | Portney |
| 6,206,931 B1 | | 3/2001 | Cook et al. |
| 6,228,113 B1 | | 5/2001 | Kaufman |
| 6,231,603 B1 | | 5/2001 | Lang et al. |
| 6,261,321 B1 | | 7/2001 | Kellan |
| 6,277,146 B1 | | 8/2001 | Peyman et al. |
| 6,280,471 B1 | | 8/2001 | Peyman et al. |
| 6,358,280 B1 | | 3/2002 | Herrick |
| 6,358,284 B1 | | 3/2002 | Fearnot et al. |
| 6,379,710 B1 | | 4/2002 | Badylak |
| 6,413,276 B1 | | 7/2002 | Werblin |
| 6,423,094 B1 | | 7/2002 | Sarfarazi |
| 6,461,384 B1 | | 10/2002 | Hoffmann et al. |
| 6,464,725 B2 | | 10/2002 | Skotton |
| 6,488,708 B2 | | 12/2002 | Sarfarazi |
| 6,530,953 B2 | | 3/2003 | Garonzik |
| 6,533,798 B2 | | 3/2003 | Greenberg et al. |
| 6,537,281 B1 | | 3/2003 | Portney |
| 6,551,354 B1 | | 4/2003 | Ghazizadeh et al. |
| 6,554,859 B1 | | 4/2003 | Lang et al. |
| 6,558,420 B2 | | 5/2003 | Green |
| 6,596,026 B1 | | 7/2003 | Gross et al. |
| 6,599,317 B1 | | 7/2003 | Joseph, III et al. |
| 6,616,691 B1 | | 9/2003 | Tran |
| 6,616,692 B1 | | 9/2003 | Glick et al. |
| 6,638,304 B2 | | 10/2003 | Azar |
| 6,645,245 B1 | | 11/2003 | Preussner |
| 6,666,892 B2 | | 12/2003 | Hiles et al. |
| 6,695,881 B2 | | 2/2004 | Peng et al. |
| 6,767,363 B1 | | 7/2004 | Bandhauer et al. |
| 6,797,004 B1 | | 9/2004 | Brady et al. |
| 6,818,017 B1 | | 11/2004 | Shu |
| 6,849,091 B1 | | 2/2005 | Cumming |
| 6,960,231 B2 | | 11/2005 | Tran |
| 6,972,032 B2 | | 12/2005 | Aharoni et al. |
| 6,991,651 B2 | | 1/2006 | Portney |
| 7,008,447 B2 | | 3/2006 | Koziol |
| 7,018,409 B2 | | 3/2006 | Glick et al. |
| 7,081,134 B2 | | 7/2006 | Cukrowski |
| 7,097,660 B2 | | 8/2006 | Portney |
| 7,101,397 B2 | | 9/2006 | Aharoni |
| 7,122,053 B2 | | 10/2006 | Esch |
| 7,125,422 B2 | | 10/2006 | Woods et al. |
| 7,150,760 B2 | | 12/2006 | Zhang |
| 7,186,266 B2 | | 3/2007 | Peyman |
| 7,198,640 B2 | | 4/2007 | Nguyen |
| 7,220,278 B2 | | 5/2007 | Peyman |
| 7,223,288 B2 | | 5/2007 | Zhang et al. |
| 7,238,201 B2 | | 7/2007 | Portney et al. |
| 7,300,464 B2 | | 11/2007 | Tran |
| 7,316,713 B2 | | 1/2008 | Zhang |
| 7,402,175 B2 | | 7/2008 | Azar |
| 7,455,691 B2 | | 11/2008 | Feingold et al. |
| 7,582,113 B2 | | 9/2009 | Terwee |
| 7,591,849 B2 | | 9/2009 | Richardson |
| 7,645,299 B2 | | 1/2010 | Koziol |
| 7,662,179 B2 | | 2/2010 | Sarfarazi |
| 7,727,277 B2 | | 6/2010 | Aharoni et al. |
| 7,780,729 B2 | | 8/2010 | Nguyen et al. |
| 7,857,850 B2 | | 12/2010 | Mentak et al. |
| 7,871,437 B2 | | 1/2011 | Hermans et al. |
| 7,918,886 B2 | | 4/2011 | Aharoni et al. |
| 7,955,383 B2 | | 6/2011 | Krivoruchko et al. |
| 7,985,253 B2 | | 7/2011 | Cumming |
| 7,993,399 B2 | | 8/2011 | Peyman |
| 7,998,198 B2 | | 8/2011 | Angelopoulos et al. |
| 8,012,204 B2 | | 9/2011 | Weinschenk, III et al. |

(56) References Cited

U.S. PATENT DOCUMENTS

| | | | |
|---|---|---|---|
| 8,034,106 | B2 | 10/2011 | Mentak et al. |
| 8,034,107 | B2 | 10/2011 | Stenger |
| 8,034,108 | B2 | 10/2011 | Bumbalough |
| 8,062,361 | B2 | 11/2011 | Nguyen et al. |
| 8,066,768 | B2 | 11/2011 | Werblin |
| 8,137,399 | B2 | 3/2012 | Glazier et al. |
| 8,152,941 | B2 | 4/2012 | Sczerzenie et al. |
| 8,167,941 | B2 | 5/2012 | Boyd et al. |
| 8,187,325 | B2 | 5/2012 | Zadno-Azizi et al. |
| 8,197,541 | B2 | 6/2012 | Schedler |
| 8,206,440 | B2 | 6/2012 | Guarnieri |
| 8,273,123 | B2 | 9/2012 | Ben Nun |
| 8,287,593 | B2 | 10/2012 | Portney |
| 8,377,124 | B2 | 2/2013 | Hong et al. |
| 8,377,125 | B2 | 2/2013 | Kellan |
| 8,430,981 | B1 | 4/2013 | Sczerzenie et al. |
| 8,480,734 | B2 | 7/2013 | Kellan et al. |
| 8,728,158 | B2 | 5/2014 | Whitsett |
| 8,758,434 | B2 | 6/2014 | Scott |
| 8,900,300 | B1 | 12/2014 | Wortz |
| 9,078,744 | B2 | 7/2015 | Van Noy |
| 9,195,073 | B2 | 11/2015 | Fritsch et al. |
| 9,220,761 | B2 | 12/2015 | Barnett |
| 9,339,375 | B2 | 5/2016 | Lee et al. |
| 9,358,103 | B1 | 6/2016 | Wortz et al. |
| 9,364,316 | B1 | 6/2016 | Kahook et al. |
| 9,414,907 | B2 | 8/2016 | Wortz et al. |
| 9,481,432 | B2 | 11/2016 | Dogliotti et al. |
| 9,486,311 | B2 | 11/2016 | Argento et al. |
| 9,681,946 | B2 | 6/2017 | Kahook et al. |
| 9,757,227 | B2 | 9/2017 | Kushlin et al. |
| 9,763,776 | B2 | 9/2017 | Lee |
| 9,833,517 | B2 | 12/2017 | Goldberg |
| 10,028,824 | B2 | 7/2018 | Kahook et al. |
| 10,052,196 | B2 | 8/2018 | Pugh et al. |
| 10,080,648 | B2 | 9/2018 | Kahook et al. |
| 10,195,018 | B2 | 2/2019 | Salahieh et al. |
| 10,350,056 | B2 | 7/2019 | Argento et al. |
| 10,406,242 | B2 | 9/2019 | Goldberg et al. |
| 10,444,541 | B2 | 10/2019 | Hyde et al. |
| 10,485,654 | B2 | 11/2019 | Brady et al. |
| 10,526,353 | B2 | 1/2020 | Silvestrini |
| 10,548,718 | B2 | 2/2020 | Salahieh et al. |
| 10,647,831 | B2 | 5/2020 | Silvestrini et al. |
| 10,736,734 | B2 | 8/2020 | Salahieh et al. |
| 10,772,721 | B2 | 9/2020 | Rao et al. |
| 10,799,340 | B2 | 10/2020 | Collins et al. |
| 10,820,985 | B2 | 11/2020 | Wortz |
| 10,842,615 | B2 | 11/2020 | Wortz et al. |
| 10,842,616 | B2 | 11/2020 | Silvestrini et al. |
| 10,856,969 | B2 | 12/2020 | Ishikawa |
| 11,076,948 | B2 | 8/2021 | Kahook et al. |
| 11,737,916 | B2 | 8/2023 | Goldberg et al. |
| 11,826,280 | B2 | 11/2023 | Barnett et al. |
| 2002/0065552 | A1 | 5/2002 | Jayaraman et al. |
| 2002/0128710 | A1 | 9/2002 | Eggleston |
| 2003/0082237 | A1 | 5/2003 | Cha et al. |
| 2003/0088253 | A1 | 5/2003 | Seil |
| 2003/0144733 | A1 | 7/2003 | Brady et al. |
| 2003/0158560 | A1 | 8/2003 | Portney |
| 2004/0010310 | A1 | 1/2004 | Peyman |
| 2004/0106993 | A1 | 6/2004 | Portney |
| 2004/0117011 | A1 | 6/2004 | Aharoni et al. |
| 2004/0148022 | A1 | 7/2004 | Eggleston |
| 2004/0236422 | A1 | 11/2004 | Zhang et al. |
| 2004/0242142 | A1 | 12/2004 | Siepser |
| 2005/0015144 | A1 | 1/2005 | Tran |
| 2005/0027354 | A1 | 2/2005 | Brady et al. |
| 2005/0125058 | A1 | 6/2005 | Cumming et al. |
| 2005/0131535 | A1 | 6/2005 | Woods |
| 2005/0187621 | A1 | 8/2005 | Brady |
| 2006/0100629 | A1* | 5/2006 | Lee ................... A61B 17/0642 |
| | | | 606/313 |
| 2006/0111776 | A1 | 5/2006 | Glick et al. |
| 2006/0286147 | A1 | 12/2006 | Salamone et al. |

| | | | |
|---|---|---|---|
| 2007/0123981 | A1 | 5/2007 | Tassignon |
| 2007/0129801 | A1 | 6/2007 | Cumming |
| 2007/0260308 | A1 | 11/2007 | Tran |
| 2008/0046077 | A1 | 2/2008 | Cumming |
| 2008/0103592 | A1 | 5/2008 | Maloney |
| 2009/0005864 | A1 | 1/2009 | Eggleston |
| 2009/0125106 | A1 | 5/2009 | Weinschenk, III et al. |
| 2010/0016964 | A1 | 1/2010 | Werblin |
| 2010/0047355 | A1 | 2/2010 | Bulte et al. |
| 2010/0204787 | A1 | 8/2010 | Noy |
| 2010/0298933 | A1 | 11/2010 | Knox et al. |
| 2011/0040378 | A1 | 2/2011 | Werblin |
| 2011/0054600 | A1 | 3/2011 | Bumbalough |
| 2011/0104052 | A1 | 5/2011 | Barnett |
| 2011/0251686 | A1 | 10/2011 | Masket |
| 2011/0307058 | A1 | 12/2011 | Beer |
| 2011/0313521 | A1 | 12/2011 | Angelopoulos |
| 2012/0078363 | A1 | 3/2012 | Lu |
| 2012/0078364 | A1 | 3/2012 | Stenger |
| 2012/0179249 | A1 | 7/2012 | Coleman |
| 2013/0184815 | A1 | 7/2013 | Roholt |
| 2013/0190868 | A1 | 7/2013 | Kahook et al. |
| 2013/0211249 | A1 | 8/2013 | Barnett |
| 2013/0225906 | A1 | 8/2013 | Zysler et al. |
| 2013/0296694 | A1 | 11/2013 | Ehlers et al. |
| 2014/0081178 | A1 | 3/2014 | Pletcher et al. |
| 2014/0085599 | A1 | 3/2014 | Etzkom |
| 2014/0085600 | A1 | 3/2014 | Pletcher et al. |
| 2014/0085602 | A1 | 3/2014 | Ho et al. |
| 2014/0087452 | A1 | 3/2014 | Liu et al. |
| 2014/0088381 | A1 | 3/2014 | Etzkom et al. |
| 2014/0098226 | A1 | 4/2014 | Pletcher et al. |
| 2014/0107777 | A1 | 4/2014 | Portney |
| 2014/0180411 | A1 | 6/2014 | Tomambe et al. |
| 2014/0192311 | A1 | 7/2014 | Pletcher et al. |
| 2014/0194710 | A1 | 7/2014 | Ho et al. |
| 2014/0194713 | A1 | 7/2014 | Liu |
| 2014/0194773 | A1 | 7/2014 | Pletcher et al. |
| 2014/0371852 | A1 | 12/2014 | Zharoni et al. |
| 2015/0230981 | A1 | 8/2015 | Kahook et al. |
| 2015/0305929 | A1 | 10/2015 | Goldberg et al. |
| 2015/0366660 | A1* | 12/2015 | Fernández Martínez .................... |
| | | | A61F 2/16015 |
| | | | 623/6.22 |
| 2016/0074154 | A1 | 3/2016 | Woods |
| 2016/0235524 | A1 | 8/2016 | Wortz et al. |
| 2016/0361156 | A1 | 12/2016 | Brown |
| 2017/0319332 | A1 | 11/2017 | Kahook et al. |
| 2017/0348095 | A1 | 12/2017 | Wortz et al. |
| 2018/0110613 | A1 | 4/2018 | Wortz et al. |
| 2018/0161153 | A1 | 6/2018 | Kahook et al. |
| 2018/0263761 | A1 | 9/2018 | Bozukova et al. |
| 2018/0368974 | A1 | 12/2018 | Kahook et al. |
| 2019/0000610 | A1* | 1/2019 | Willis ..................... A61F 9/007 |
| 2019/0021848 | A1 | 1/2019 | Kahook et al. |
| 2019/0117382 | A1 | 4/2019 | Kahook |
| 2019/0183633 | A1 | 6/2019 | Cable, Ii |
| 2019/0321219 | A1 | 10/2019 | Ostermeier et al. |
| 2020/0022840 | A1 | 1/2020 | Kahook et al. |
| 2021/0161652 | A1 | 6/2021 | Barnett |
| 2021/0161655 | A1 | 6/2021 | Kascheke et al. |
| 2021/0298762 | A1 | 9/2021 | Jun et al. |
| 2021/0378681 | A1 | 12/2021 | Dennewill et al. |
| 2022/0304799 | A1* | 9/2022 | Buchheister .......... A61F 2/1624 |
| 2025/0152415 | A1 | 5/2025 | Goldberg et al. |
| 2025/0152506 | A1 | 5/2025 | Goldberg et al. |

FOREIGN PATENT DOCUMENTS

| | | |
|---|---|---|
| CA | 2350795 C | 7/2006 |
| CA | 2407432 C | 1/2007 |
| CA | 2480772 C | 11/2008 |
| CA | 2959354 C | 8/2018 |
| CA | 3095098 A1 | 10/2019 |
| CN | 101164621 B | 5/2010 |
| CN | 104936553 B | 3/2017 |
| CN | 107625216 A | 1/2018 |
| CN | 107205812 B | 11/2019 |
| CN | 107961101 B | 12/2019 |

(56) References Cited

FOREIGN PATENT DOCUMENTS

| | | | |
|---|---|---|---|
| DE | 102016221371 A1 | 5/2018 |
| DE | 102017112085 A1 | 12/2018 |
| EP | 1138282 A1 | 10/2001 |
| EP | 1202684 B1 | 4/2003 |
| EP | 1457170 A1 | 9/2004 |
| EP | 1200019 B1 | 9/2005 |
| EP | 2042124 A1 | 4/2009 |
| EP | 1278483 B1 | 8/2011 |
| ES | 2233049 T3 | 6/2005 |
| ES | 2300278 T3 | 6/2008 |
| ES | 2379781 T3 | 5/2012 |
| JP | S6222641 A | 1/1987 |
| JP | S6389154 A | 4/1988 |
| JP | H06165793 A | 6/1994 |
| JP | 2003524503 A | 8/2003 |
| JP | 4261488 B2 | 4/2009 |
| JP | 4486122 B2 | 6/2010 |
| JP | 4511533 B2 | 7/2010 |
| JP | 2012040326 A | 3/2012 |
| JP | 5379152 B2 | 12/2013 |
| JP | 5705529 B2 | 4/2015 |
| JP | 6030089 B2 | 11/2016 |
| JP | 6270739 B2 | 1/2018 |
| JP | 6499307 B2 | 4/2019 |
| JP | 2019520886 A | 7/2019 |
| JP | 6779262 B2 | 11/2020 |
| KR | 100913267 B1 | 8/2009 |
| WO | 94/28825 A1 | 12/1994 |
| WO | 2000050100 A1 | 8/2000 |
| WO | 2001064136 A3 | 9/2001 |
| WO | 2004093643 A2 | 11/2004 |
| WO | 2005084587 A3 | 9/2005 |
| WO | 2006050171 A2 | 5/2006 |
| WO | 2007123633 A1 | 11/2007 |
| WO | 2008094518 A1 | 8/2008 |
| WO | 2009073193 A2 | 6/2009 |
| WO | 2010002215 A2 | 1/2010 |
| WO | 2012023133 A1 | 2/2012 |
| WO | 2013112589 A1 | 8/2013 |
| WO | 2013158942 A1 | 10/2013 |
| WO | 2014197170 A1 | 12/2014 |
| WO | 2014204575 A1 | 12/2014 |
| WO | 2015195825 A1 | 12/2015 |
| WO | 2016022995 A2 | 2/2016 |
| WO | 2016126285 A1 | 8/2016 |
| WO | 20160122805 A1 | 8/2016 |
| WO | 2020028021 A1 | 2/2020 |
| WO | 2020028022 A1 | 2/2020 |

OTHER PUBLICATIONS

Chan, L.; Moster, M. R.; Bicket, A. K.; Sheybani, A.; Sarkisian, S. R.; Samuelson, T. W.; Ahmed, I. I. K.; Miller-Ellis, E.; Smith, O. U.; Cui, Q. N. New Devices in Glaucoma. Ophthalmol Ther 2023, 12 (5), 2381-2395. DOI: 10.1007/s40123-023-00780-3 From NLM PubMed-not-Medline.

Reinstein, D. Z.; Yap, T. E.; Archer, T. J.; Gobbe, M.; Silverman, R. H. Comparison of Corneal Epithelial Thickness Measurement Between Fourier-Domain OCT and Very High-Frequency Digital Ultrasound. J Refract Surg 2015, 31 (7), 438-445. DOI: 10.3928/1081597X-20150623-01 From NLM Medline.

Ursea, R.; Feng, M.; Urs, R.; RoyChoudhury, A.; Silverman, R. H. Comparison of artemis 2 ultrasound and Visante optical coherence tomography corneal thickness profiles. J Refract Surg 2013, 29 (1), 36-41. DOI: 10.3928/1081597X-20121126-01 From NLM Medline.

Urs, R.; Lloyd, H. O.; Reinstein, D. Z.; Silverman, R. H. Comparison of very-high-frequency ultrasound and spectral-domain optical coherence tomography corneal and epithelial thickness maps. J Cataract Refract Surg 2016, 42 (1), 95-101. DOI: 10.1016/j.jcrs.2015.07.038 From NLM Medline.

Bacharach, J.; Tatham, A.; Ferguson, G.; Belalcazar, S.; Thieme, H.; Goodkin, M. L.; Chen, M. Y.; Guo, Q.; Liu, J.; Robinson, M. R.; et al. Phase 3, Randomized, 20-Month Study of the Efficacy and Safety of Bimatoprost Implant in Patients with Open-Angle Glaucoma and Ocular Hypertension (Artemis 2). Drugs 2021, 81 (17), 2017-2033. DOI: 10.1007/s40265-021-01624-9 From NLM Medline.

Belamkar, A.; Harris, A.; Zukerman, R.; Siesky, B.; Oddone, F.; Verticchio Vercellin, A.; Ciulla, T. A. Sustained release glaucoma therapies: Novel modalities for overcoming key treatment barriers associated with topical medications. Ann Med 2022, 54 (1), 343-358. DOI: 10.1080/07853890.2021.1955146 From NLM Medline.

Ghosn, C.; Rajagopalan, L.; Ugarte, S.; Mistry, S.; Orilla, W.; Goodkin, M. L.; Robinson, M. R.; Engles, M.; Dibas, M. Intraocular Pressure-Lowering Efficacy of a Sustained-Release Bimatoprost Implant in Dog Eyes Pretreated with Selective Laser Trabeculoplasty. J Ocul Pharmacol Ther 2022, 38 (4), 311-318. DOI: 10.1089/jop.2021.0104 From NLM Medline.

Lee, S. S.; Dibas, M.; Almazan, A.; Robinson, M. R. Dose-Response of Intracameral Bimatoprost Sustained-Release Implant and Topical Bimatoprost in Lowering Intraocular Pressure. J Ocul Pharmacol Ther 2019, 35 (3), 138-144. DOI: 10.1089/jop.2018.0095 From NLM Medline.

Lee, S. S.; Robinson, M. R.; Weinreb, R. N. Episcleral Venous Pressure and the Ocular Hypotensive Effects of Topical and Intracameral Prostaglandin Analogs. J Glaucoma 2019, 28 (9), 846-857. DOI: 10.1097/IJG.0000000000001307 From NLM Medline.

Medeiros, F. A.; Walters, T. R.; Kolko, M.; Coote, M.; Bejanian, M.; Goodkin, M. L.; Guo, Q.; Zhang, J.; Robinson, M. R.; Weinreb, R. N.; Group, A. S. Phase 3, Randomized, 20-Month Study of Bimatoprost Implant in Open-Angle Glaucoma and Ocular Hypertension (Artemis 1). Ophthalmology 2020, 127 (12), 1627-1641. DOI: 10.1016/j.ophtha.2020.06.018 From NLM Medline.

Shirley, M. Bimatoprost Implant: First Approval. Drugs Aging 2020, 37 (6), 457-462. DOI: 10.1007/s40266-020-00769-8 From NLM Medline.

Weinreb, R. N.; Bacharach, J.; Brubaker, J. W.; Medeiros, F. A.; Bejanian, M.; Bernstein, P.; Robinson, M. R. Bimatoprost Implant Biodegradation in the Phase 3, Randomized, 20-Month Artemis Studies. J Ocul Pharmacol Ther 2023, 39 (1), 55-62. DOI: 10.1089/jop.2022.0137 From NLM Medline.

Silverman, R. H. Focused ultrasound in ophthalmology. Clin Ophthalmol 2016, 10, 1865-1875. DOI: 10.2147/OPTH.S99535 From NLM PubMed-not-Medline.

Reinstein, D. Z.; Archer, T. J.; Gobbe, M.; Silverman, R. H.; Coleman, D. J. Epithelial thickness after hyperopic LASIK: three-dimensional display with Artemis very high-frequency digital ultrasound. J Refract Surg 2010, 26 (8), 555-564. Doi: 10.3928/1081597X-20091105-02 From NLM Medline.

Reinstein, D. Z.; Gobbe, M.; Archer, T. J.; Silverman, R. H.; Coleman, D. J. Epithelial, stromal, and total corneal thickness in keratoconus: three-dimensional display with artemis very-high frequency digital ultrasound. J Refract Surg 2010, 26 (4), 259-271. DOI: 10.3928/1081597X-20100218-01 From NLM Medline.

Eugene de Juan Jr et al., "Retinal Tacks," American Journal of Ophthalmology, vol. 99, issue 3, Mar. 1985, pp. 272-274.

Luca Mautone et al., "Retinal Tacks for Complicated Retinal Detachment: Retinal Tacks in the Times of Modern Small-Gauge Vitrectomy," Journal of Ophthalmology, published online Mar. 3, 20221, PMC8991402.

Notice of Allowance issued in U.S. Appl. No. 17/471,496, mailed Apr. 20, 2022, 13 pages.

Invitation to Pay Additional Fees and, Where Applicable, Protest Fee issued in International Application No. PCT/US2022/043014, mailed Jan. 10, 2023, 12 pages.

International Search Report and Written Opinion issued in International Application No. PCT/US2022/043014, mailed Apr. 5, 2023, 19 pages.

* cited by examiner

FIG. 3A             FIG. 3B

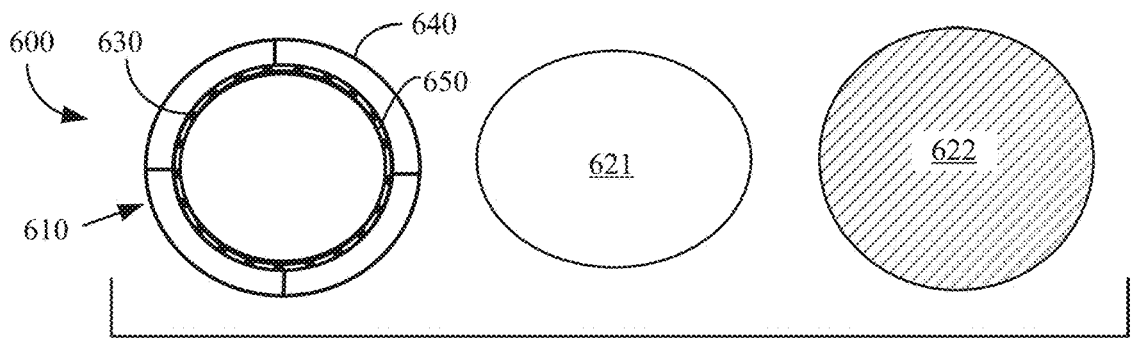
FIG. 6A
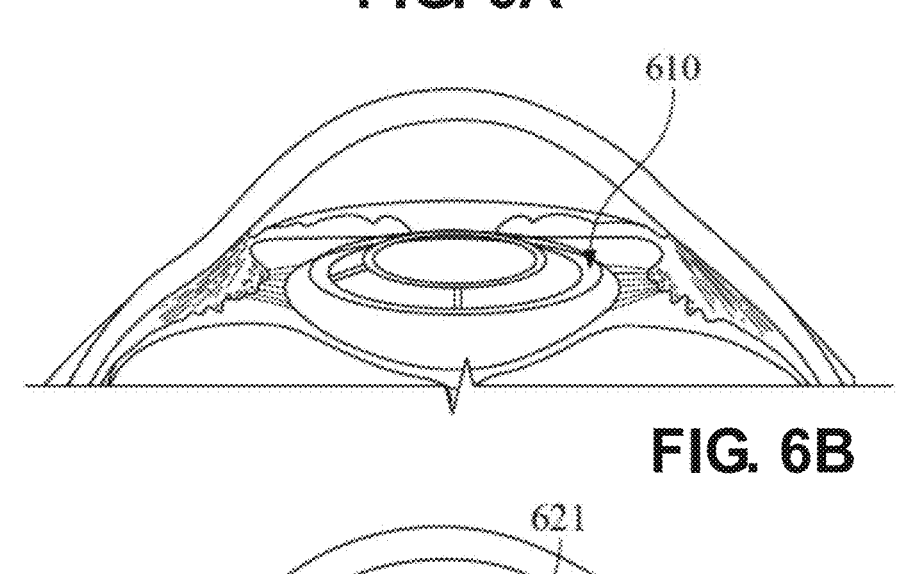
FIG. 6B
FIG. 6C
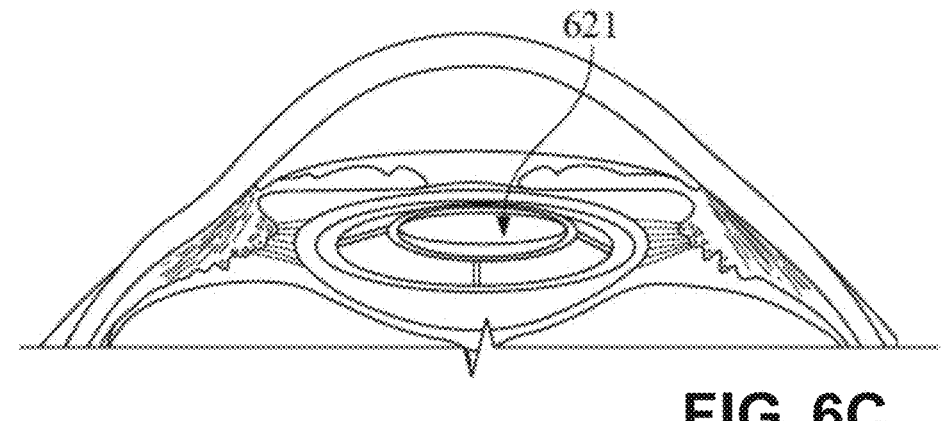
FIG. 6D

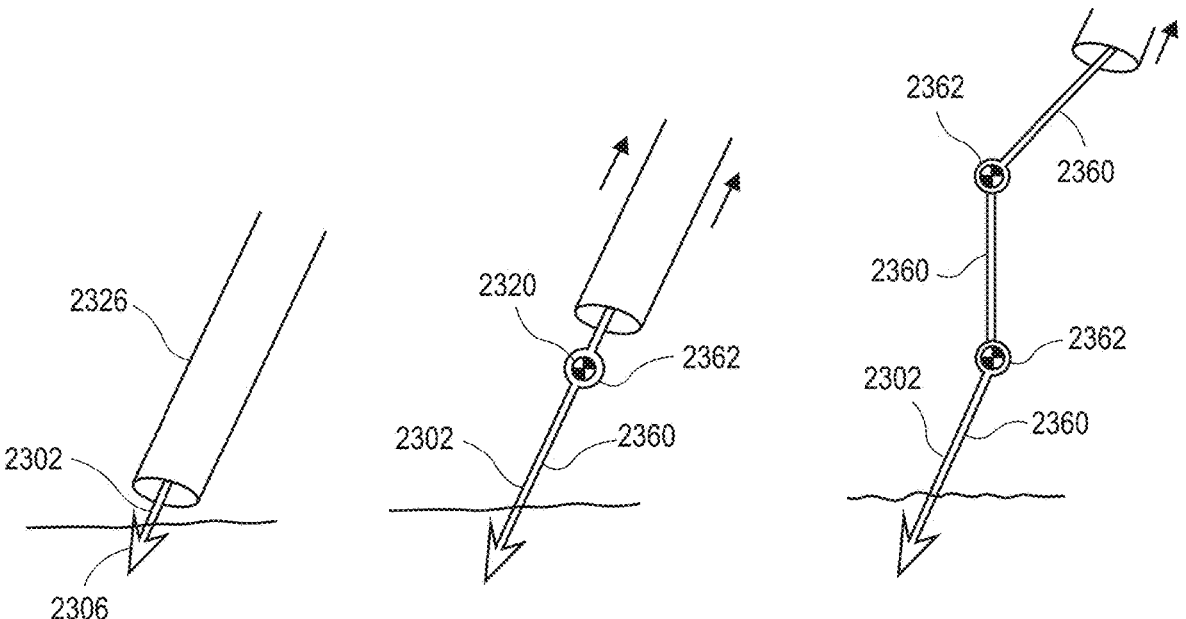
FIG. 23A          FIG. 23B          FIG. 23C
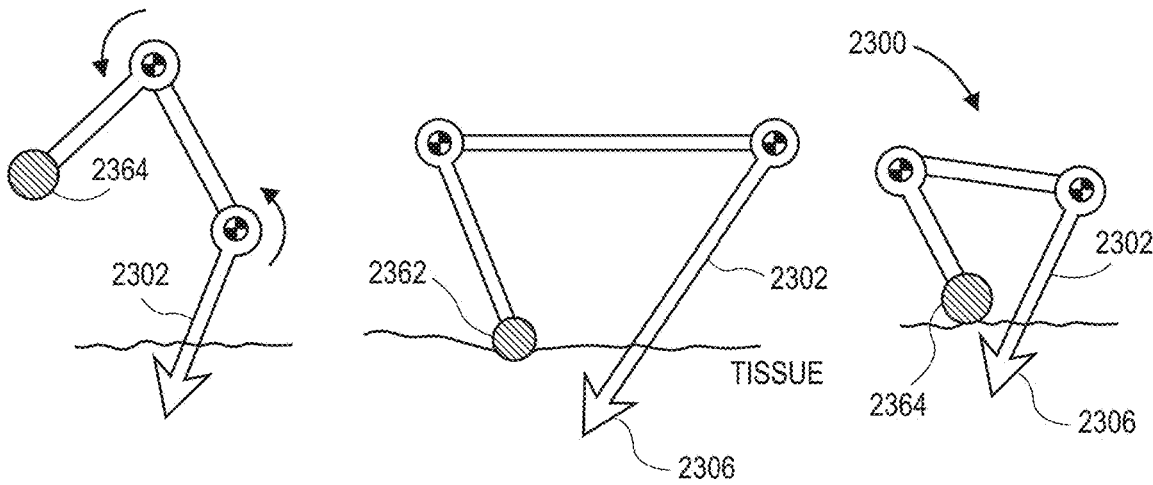
FIG. 23D          FIG. 23E          FIG. 23F

EXCHANGEABLE OPTICS AND THERAPEUTICS USING MAGNETIC TACKS

CROSS-REFERENCES TO RELATED APPLICATIONS

This application is a continuation-in-part (CIP) application of U.S. application Ser. No. 17/839,407, filed Jun. 13, 2022, which is a continuation application of U.S. application Ser. No. 17/471,496, filed Sep. 10, 2021, the contents of which are hereby incorporated in their entireties for all purposes.

BACKGROUND

1. Field of the Art

Embodiments of the present invention generally relate to repeated and reversible fastening means for implants within an eye, including multipart intraocular lens (IOL) assemblies. Specifically, they relate to a permanent magnetic tack or screw support structures, or a sclera buckle with permanent magnets, to which optics (e.g., IOLs and contact lenses) may be magnetically tethered and suspended within the eye and/or depot drug delivery formulations held in place.

2. Description of the Related Art

An intraocular lens (IOL) is a lens that is implanted in the eye. IOLs come in phakic, designed to be implanted without performing cataract surgery, and pseudophakic, designed to be implanted in conjunction with cataract surgery, varieties. A phakic IOL has the ability to reside in the sulcus space between the capsular bag and the iris or alternatively can reside in the anterior chamber, between the iris and cornea. The most commonly employed pseudophakic IOL is a posterior chamber IOL that includes haptics that enable the lens to be held in place in the capsular bag inside the eye. Implantation of an IOL is often carried out by an eye surgeon in a surgical center, but may be also be performed at an ophthalmologist's office in an in office surgical suite. In-office procedures are particularly common with phakic IOLs, much in the same way laser refractive surgeries are typically in-office. The field of pseudophakic IOLs is increasingly addressing the issue of presbyopia, which is the case where someone is not able to see both at distance and near. Presbyopia is not an indication for insurance coverage of cataract surgery currently.

As the field matures, it is likely IOLs will be increasingly utilized to address presbyopia, instead of glare and blurred vision even with glasses or some form of wearable refractive correction which is the current indication. To achieve the quality of vision of laser refractive surgery and to enable incremental changes to the lens as the technology improves, a means of fully customizable and upgradeable IOL design is sorely needed. Refractive cataract surgery replaces the natural eye lens with an advanced multi-focal or extended-depth-of-focus (EDOF) IOL. Refractive cataract surgery has not achieved the precision of corneal refractive surgery, such as LASIK (laser-assisted in situ keratomileusis), which can be individualized to high precision. Moreover, there currently is a lack of wave-front guided precision in cataract extraction and IOL implantation.

A wavefront-guided approach, otherwise known as ray traced approach, refers to an ablation profile that considers preoperative higher-order aberrations, where the final goal is to avoid inducing aberrations and to eliminate some that exist. Using ray-tracing, an individualized three-dimensional (3D) eye model can be generated that determines an ablation pattern necessary for laser vision correction and light adjustable lens adjustments. The current state of the art involves iris tracking. The iris is a dynamic, changing structure. Ray-tracing is commonly employed with laser refractive surgery such as LASIK and PRK (photorefractive keratectomy), as all variables in the eye are known. The laser ablation profile is computed preoperatively according to the results of aberrometry and is transferred to a laser system for use, for example, during surgery. The only modification made to the eye is to the shape of the cornea. Currently this is an elusive task in cataract surgery for two reasons. Principally, the effective lens position, where the IOL ends up in the eye, is hard to determine. Small changes in the anterior posterior position make large changes in the total power of the lens. In addition, zonular weakness induced by the surgery and change in corneal astigmatism made by the cataract main incision can respectively change the lens position and the corneal curvature. Moreover, any customized, astigmatism and higher order aberration correction on the IOL is precluded a priori by potential shifting of the IOL within the capsular bag in the X, Y, Z planes.

Outside of the inability to provide wavefront or ray-trace guided IOL optimization, current IOL systems do not enable ease of correction if a non-optimal IOL is placed, nor do they allow for ease of upgradeability. One current clinical exception to this is a light adjustable lens from RxSight, Aliso Viejo, California, USA. Currently the light adjustable lens uses two haptics as a means of determining the lens center. These haptics, much like the iris, dynamically move. They also require broad dilation for visualization, which creates other clinical issues. IOL exchange is a challenging procedure that, even in the most skilled surgeon's hands, results in significant trauma to the ocular structures. This is so much so that IOL exchange is commonly viewed as a last resort. However, repeated removal and replacement of a conventional IOL may not be an easy procedure and can result in complications. For example, IOL exchange with the conventional IOLs requires dissection of the capsular bag and retrieval of an unfolded lens through the cornea or sclera. Either retrieval approach (through the cornea or through the sclera) is highly traumatic to the eye and its delicate structures. Instead of exchanging IOLs, most surgeons will perform LASIK or other laser refractive procedure to the cornea. This also is not infinitely repeatable as corneal tissue is ablated at each procedure. In a similar vein, even a light adjustable lens has only a finite number of adjustments available. Unlike laser vision correction in which repeated laser correction can lead to a host of complications including corneal ectasia and epithelial ingrowth, laser vision correction can also induce ocular surface disease in even young patients, and thus is less than ideal in many of the older individuals undergoing cataract surgery.

A need exists for a system that enables relatively unlimited exchangeable optics and therapeutics as well as wavefront guided or ray-traced lens optimization.

BRIEF SUMMARY

Exchangeable optics and therapeutics, and means for fastening them, are described that can enable progressive application and exchanges of lenses and/or therapeutics in or on the eye.

An exchangeable optics system can include an intraocular base that can be fixed within an eye. The intraocular base includes one or more couplers and a supporting structure.

The one or more couplers can include magnetic material or other releasable fixation material or structures. For example, the releasable couplers can be in the form of a hook and loop coupler, a memory material fixation element such as what is utilized for tagging guns for affixing tags to clothing, a button fastener, a screw-type fastener, a hinge-based fastener similar to a cuff link, a suction cup based mechanism, an adhesive, or any other means of reversible fixation.

Biocompatible permanent magnets may be used for reversible fixation. A magnetic screw or tack can involve a sharp element that punctures into and anchors in the sclera. It may also have petal-like mechanical stress dispersal elements that pop open under the conjunctiva. These petals, in conjunction with the anchor in the sclera, help prevent the anchor in the sclera from moving. They also distribute forces from the fixation element over a broader area to reduce local tissue trauma. In addition, the elements can include fiducials that enable co-registration of serial photos or scans of the body. The fiducial can be made of a material that emits fluorescence or is bioluminescent, and/or are detectable by optical coherence tomography (OCT), ultrasound, x-ray, and/or magnetic resonance imaging (MRI). In particular, fiducials that are not visible in the spectrum perceivable by the human eye may be ideal for fiducials either in the visual axis or from an aesthetic standpoint, beneath the conjunctival surface. Alternatively, the subconjunctival fiducial can be white to match the natural color of the conjunctiva.

Magnetic fixation is particularly attractive as the base element to which optics can be coupled in the capsular bag. The magnetic or ferromagnetic metal optic can couple through magnetic force through the anterior capsular bag without physically, directly contacting the IOL in the bag. Magnetic attraction is also an ideal mechanism as it allows for a secondary optic to be disengaged from a primary optic or base with minimal force. Accordingly for magnetic and other types of releasable couplers, it can be important to consider damage to delicate zonules that hold the capsular bag. The supporting structure can include haptics and a main structure that physically supports an exchangeable optic or therapeutic that is coupled via the one or more couplers. In some cases, the intraocular base can include a fixed lens within or on the main structure.

Optics may be suspended with guy wire tethers that are magnetically attached to anchors within firmer portions of the eye. The tethers can include ends comprised of magnetic material or metals that are attracted to magnets. The tether ends and anchors may be affixed across structures in the eye in which no direct physical contact occurs. The tethers can be lengthened or shorted using magnets along their lengths to double back segments.

The same magnetic tack can be used to hold a contact lens or depot drug delivery device on the surface of the eye and an intraocular lens implant and an intraocular depot implant in the eye. The magnetic tack can serve a dual function as a fiducial that can be detected visually or through a variety of imaging devices to understand the position of the eye and allow for precise image overlays. To achieve certain outcomes, such as ray-traced changes to a lens, the ray-traced imaging should be precisely overlayed and applied in the exact same orientation in the eye. The magnetic tack cannot only act to hold an object precisely in one location, but it also can allow one to understand the relationship of the affixed object to scans capable of imaging the fiducial. In a simpler embodiment than ray-tracing, simply a toric contact lens can be held in one orientation by replacing its ballast weight with a small magnet that binds to a tack. A ray-traced contact lens can then be printed that directly affixes to the magnet. A similar approach can be used for ray-traced custom optics that can be secondarily introduced based on ray-tracing using the fiducial on the base, magnetic tack, and lens for reference.

Some embodiments of the present invention are related to an exchangeable optics system including an intraocular base comprising one or more couplers for releasably coupling to an exchangeable optic or therapeutic, and a supporting structure for physically supporting the exchangeable optic or therapeutic when coupled to the intraocular base via the one or more couplers.

The exchangeable optics system can further include the exchangeable optic, wherein the exchangeable optic comprises one or more corresponding couplers. The intraocular base can further comprise a secondary lens on or within the supporting structure. The exchangeable optic can comprise a wavefront guided or ray traced optic, and the secondary lens provides primary power. The exchangeable optics system can include a first set of fiducials on the intraocular base, and a second set of fiducials on the exchangeable optic.

In the setting of a fiducial in the optical axis of a patient, far-red fluorescent reporters or any other signal outside of the main visual spectrum can enable fiducial visualization even central to the visual axis. Much like the lume of a watch, the far red reporter can be charged with one wavelength of light to emit another wavelength of light. For fiducials beneath the conjunctiva, fluorescent reporters even in the visual spectrum can be employed. To maximize the fluorescence, similar to watch lume the fiducial can be charged by an external light to emit a fluorescent signal.

Each of the one or more couplers can comprise magnetic material. The one or more couplers can comprise a magnetic ring on the supporting structure. The supporting structure can comprise haptics for fixedly coupling the intraocular base within an eye, and a main structure. The one or more couplers can be located on a periphery of the main structure. The supporting structure can comprise an intraocular lens, wherein the main structure comprises a lens of the intraocular lens. The exchangeable optic can further comprise fiducials on the main structure.

The exchangeable optics system can further include the therapeutic. The therapeutic can comprise a magnetic particle. The magnetic particle can comprise a magnetite core with a polymer coating and polyethylene glycol shell. The magnetic particle can comprise a liposome shell, a magnetic ferrofluid within the liposome shell, and a drug or therapeutic core within the liposome shell. The one or more couplers can comprise magnetic material on a haptic of the supporting structure or a magnetic ring on the supporting structure.

Some embodiments are related to an exchangeable optic comprising a lens, and one or more magnets on the lens.

The exchangeable optic can further include a hole within a periphery of the lens and/or fiducials on the lens. One or more magnets can be disposed in alignment for coupling to corresponding one or more couplers of an intraocular base.

Some embodiments of the present invention are related to an anchor apparatus for soft biological tissue, the apparatus including a shaft less than 2 to 3 millimeters in diameter and having an axis configured to be normal to a surface of soft tissue, and a sharp protrusion from the shaft configured to pierce and embed in soft tissue wherein the shaft is comprised of a biocompatible permanent magnet.

The apparatus can further include a deployable flange surrounding the shaft, the flange configured to move between a stowed configuration, in which the flange is wrapped around the axis, to a deployed configuration, in which the flange expands outward to surround the shaft. It can include a superelastic material configured to move the flange from the linear stowed configuration, in which the flange is squeezed into a cylinder around the axis, to the deployed configuration, in which the flange expands outward to a circle surrounding the shaft. The flange can include a wire skeleton having continuous loops and no sharp wire end. The flange can further include a continuous polymer sheet over the wire skeleton. The flange can further include a resilient polymer coating the wire skeleton. The superelastic material can include nitinol wire.

The sharp protrusion can be a screw thread, and the shaft can include a notch for transferring torque from an insertion tool to the shaft and screw thread. The sharp protrusion can include a barb. The apparatus can further include a fiducial shape connected with the shaft.

Embodiments can be related to an intraocular lens system comprising the anchor apparatus, a lens, and a suspension cable having an end configured to attach with the lens and an opposite magnetic end or a ferromagnetic end configured to magnetically mate with the permanent magnet.

The end configured to attach with the lens can include a magnet. The magnetic end can include a ring-shaped magnet through which a wire is wrapped and fastened. The lens can include a wavefront guided or ray traced optic.

Some embodiments are related to a magnetic scleral buckle anchor apparatus for an eye, the apparatus comprising a scleral buckle, and biocompatible, permanent magnets attached to the scleral buckle, the magnets spaced from each other as to be symmetrically located around a circumference of a sclera when the scleral buckle is affixed around an eye. The apparatus can further comprise a fiducial shape attached to the scleral buckle.

Embodiments are related to an intraocular lens system, the system comprising the anchor apparatus, a lens, and a suspension cable having an end configured to attach with the lens and an opposite magnetic end or a ferromagnetic end configured to magnetically mate with one of the permanent magnets.

The end configured to attach with the lens can include a magnet. The magnetic end can include a ring-shaped magnet through which a wire is wrapped and fastened. The lens can include a wavefront guided or ray traced optic This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 3A is a perspective view of an exchangeable optic with clips for coupling to an intraocular base.

FIG. 3B is a top view of the exchangeable optic of FIG. 3A.

FIG. 6A is an exploded view of an exchangeable optics system having multiple stacked lenses.

FIG. 6B illustrates the exchangeable optics system of FIG. 6A within the sulcus space of an eye.

FIG. 6C illustrates the exchangeable optics system of FIG. 6B to which a first optic is attached.

FIG. 6D illustrates the exchangeable optics system of FIG. 6B to which a second optic is stacked.

FIG. 23A illustrates insertion of a barb of a hinged anchor in accordance with an embodiment.

FIG. 23B illustrates withdrawal of a cannula past a first hinge of the hinged anchor of FIG. 23A.

FIG. 23C illustrates withdrawal of a cannula past a second hinge of the hinged anchor of FIG. 23A.

FIG. 23D illustrates swiveling hinges of the hinged anchor of FIG. 23A.

FIG. 23E illustrates a magnetic end attracted to a magnetic barb of the hinged anchor of FIG. 23A.

FIG. 23F illustrates the magnetic end seating near the magnetic barb of FIG. 23E.

DETAILED DESCRIPTION

Exchangeable optics and therapeutics are described that can enable progressive application and exchanges of lenses and/or therapeutics in the eye.

Figure 1A:
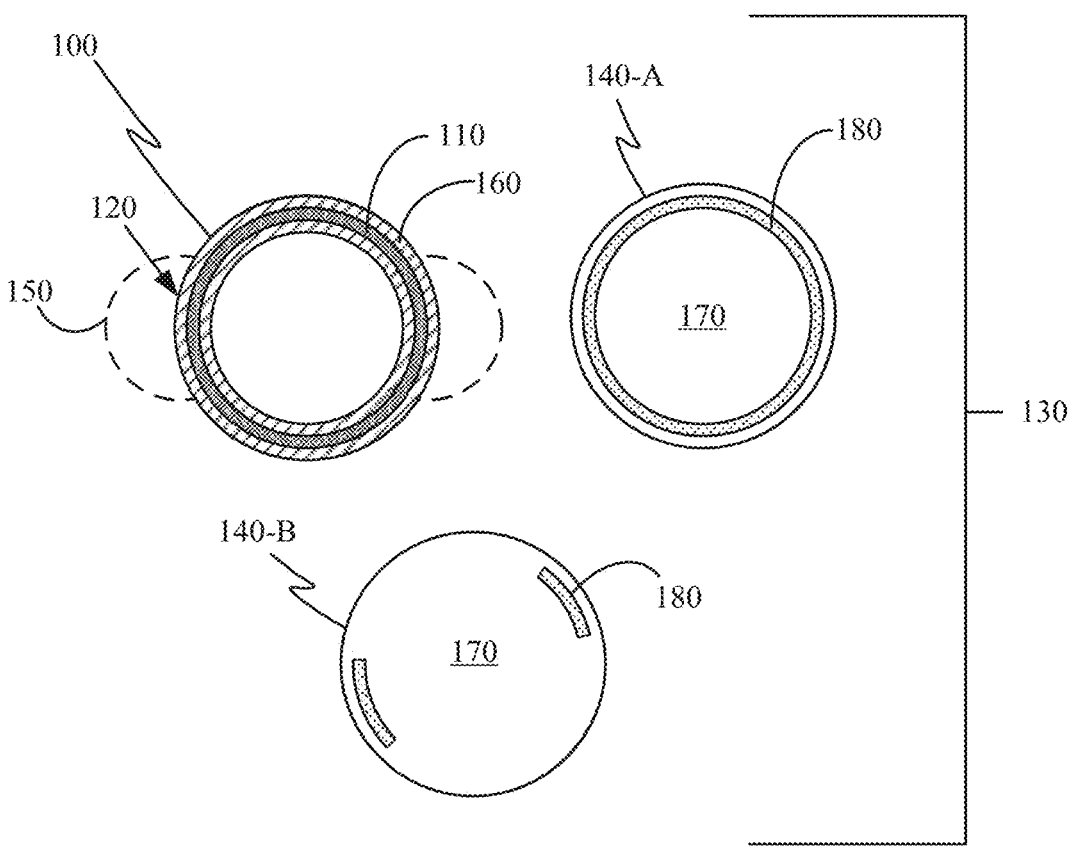
FIG. 1A illustrates an exchangeable optics system for an implantable intraocular lens.
Figure 1B:
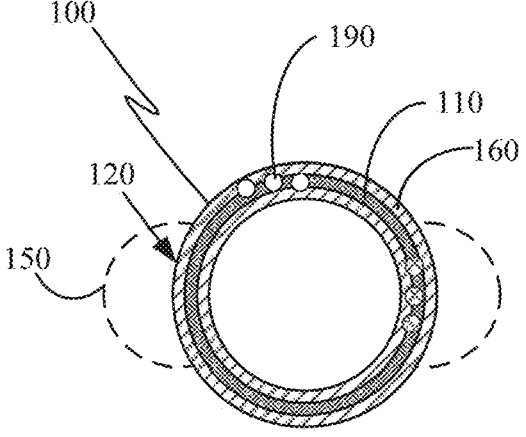
FIG. 1B illustrates an exchangeable optics system suitable for the application of therapeutics.

FIGS. 1A and 1B illustrate exchangeable optics systems suitable for an implantable intraocular lens and application of therapeutics. As shown in FIGS. 1A and 1B, Exchangeable optics systems include an intraocular base 100 that can be fixed within an eye. The intraocular base 100 includes one or more couplers (e.g., coupler 110) and a supporting structure 120. The one or more couplers can include magnetic material or other releasable fixation material or structures. In this example, a single ring-shaped coupler 110 is shown.

Referring to FIG. 1A, an exchangeable optics system 130 can include an intraocular base 100 that supports an exchangeable optic (e.g., 140-A, 140-B) and can be fixed within the eye. As mentioned above, the intraocular base 100 can include one or more couplers (e.g., coupler 110) and a supporting structure 120. The one or more couplers, in this case, ring-shaped coupler 110, are used to releasably couple the intraocular base 100 to the exchangeable optic 140-A, 140-B. The supporting structure 120 can include haptics 150 for suturing or otherwise fixing the intraocular base 100 in the eye and a main structure 160 (which may be a circular substructure), which can be used to physically support an exchangeable optic 140-A, 140-B directly or indirectly via the one or more couplers.

The haptics 150 can be any suitable structure enabling the intraocular base 100 to be fixed within the eye. Various examples are shown in FIGS. 6A, 7A, 10, 11A, and 12A-12D.

In the illustrated scenario, the main structure 160 is open in the center such that the exchangeable optic 140-A, 140-B rests on a proximal surface at the perimeter of the intraocular base 100. In other implementations, the main structure 160 has a transparent surface over which the exchangeable optic 140-A, 140-B rests. The supporting structure 120 can also optionally include a lens or IOL (not shown) within or on the main structure 160. In some cases, the supporting structure 120 can include one or more protrusions that can be used to extend up through a hole in the capsular bag of the eye (see e.g., extensions 222 of FIG. 2B and tension ring extensions 1125 of FIG. 11A). In some of such cases, a coupler can be disposed at an end of a protrusion. This coupler may be the coupler for the base or an additional coupler for the base.

Figures 9A, 9B:
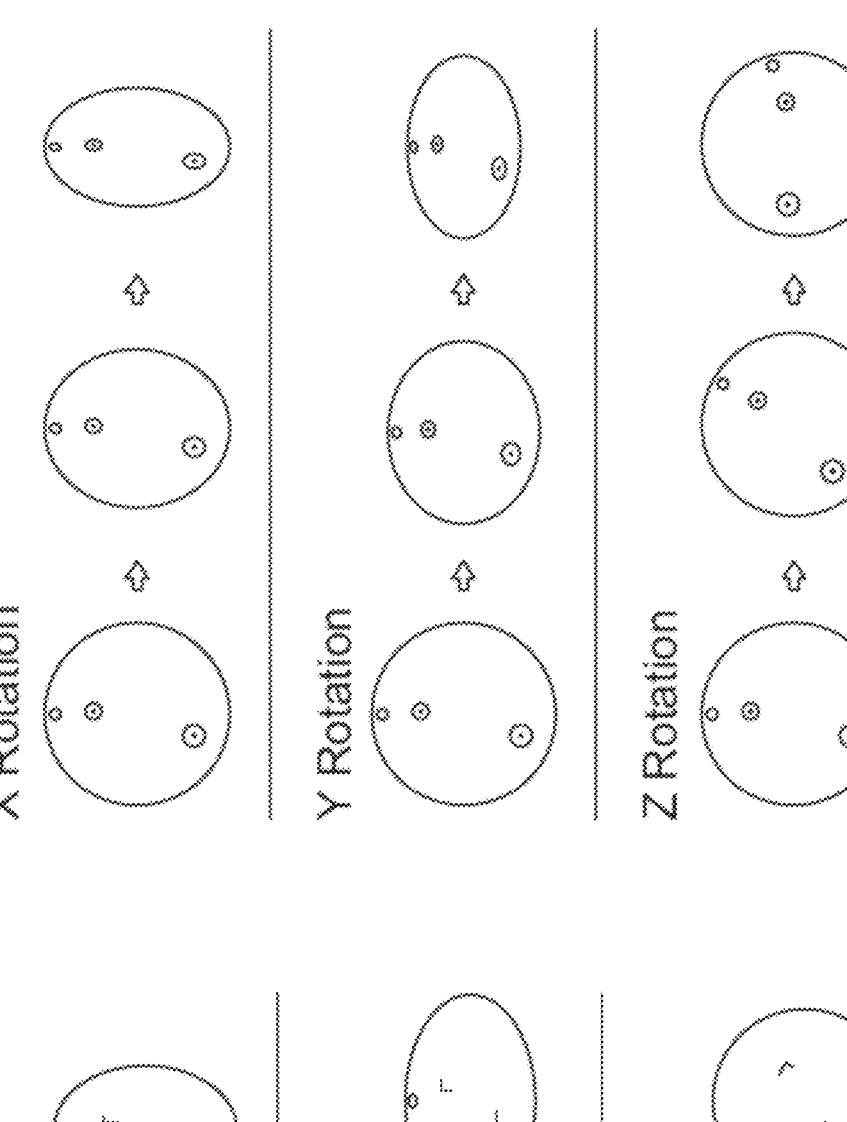
FIG. 9A shows L-shaped fiducials printed on a lens or haptic that can enable precise orientation of three-dimensional rotation of an optic or haptic FIG. 9B show bullseye fiducial designs printed on a lens or haptic.

The exchangeable optic 140-A, 140-B can include a lens 170 and one or more corresponding couplers 180. For application of the exchangeable optics system 130, the intraocular base 100 can be deployed in an eye. One of the exchangeable optics 140-A, 140-B can then be deployed, oriented/aligned, and coupled to the intraocular base 100 using the couplers 110, 180 (illustrated as magnets/magnetic material). Alignment can involve radial alignment with respect to either the intraocular base, the eye, or some structure within the eye. The one or more exchangeable optics (e.g., optic 140-A, 140-B) can include fiducials to aid in radial alignment, such as seen in FIGS. 9A and 9B. Alignment can also involve depth alignment with respect to either the intraocular base, the eye, or some structure within the eye.

In some cases, there are more or fewer "corresponding couplers" 180 than there are couplers 110 of the intraocular base 100. For example, the couplers of the base may be point couplers while the couplers of the optic may be a single ring shape. In the illustrated scenario, one exchangeable optic 140-A is shown with a single corresponding coupler 180, which is in the shape of a ring; and the other exchangeable optic 140-B is shown with two corresponding couplers 180 that are positioned to both couple to the ring-shaped coupler 110 of the intraocular base 100. The coupling between the intraocular base 100 and the exchangeable optic 140-A, 140-B can be accomplished in a variety of ways, for example, magnetically, using friction, or chemically. In the illustrated scenario, magnetic coupling is shown.

Of course, while a ring-shape coupler 110 is one example, the one or more couplers at the intraocular base may be two couplers formed of magnetic material such that the coupling is accomplished using a two-point coupling where a first of the one or more couplers of the intraocular base is disposed at a proximal surface (i.e., the surface facing outward from the eye) on one side of the intraocular base and a second of the one or more couplers is disposed at the proximal surface on another side of the intraocular base. The corresponding one or more couplers would then be disposed at the exchangeable optic in a manner to orient and couple the exchangeable optic to the base. For example, the corresponding one or more couplers would be disposed in alignment for coupling to the one or more couplers of the intraocular base.

As mentioned above, the one or more couplers 110 and the corresponding one or more couplers 180 can be formed of magnetic material. The magnetic material can be any suitable ferromagnetic or ferrimagnetic material. The magnetic material is sized and shaped so as to minimize or avoid susceptibility to strong external magnetic fields such as MRI (e.g., avoiding/minimizing movement or interference with imaging).

It should be understood that although the examples contained herein make reference to the couplers being magnets or magnetic, other types of releasable couplers can be used (e.g., chemical, mechanical, or friction based) in certain implementations. The use of magnetic couplers also enable certain therapeutics to be applied.

Indeed, referring to FIG. 1B, the same intraocular base 100 can be used to apply therapeutics 190. In the illustrated scenario, therapeutics 190 can be coupled to the intraocular base 100. In some cases, the therapeutics 190 are applied once the intraocular base 100 is deployed in the eye. In some cases, the therapeutics 190 may be applied before original deployment and then optionally reapplied after deployment.

Figure 2A:
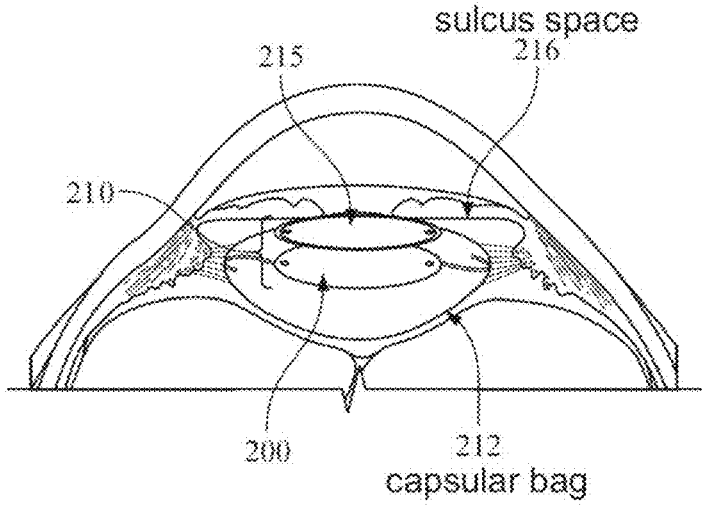
FIG. 2A illustrates an exchangeable optics system with in intraocular base within a capsular bag of an eye.
Figure 2B:
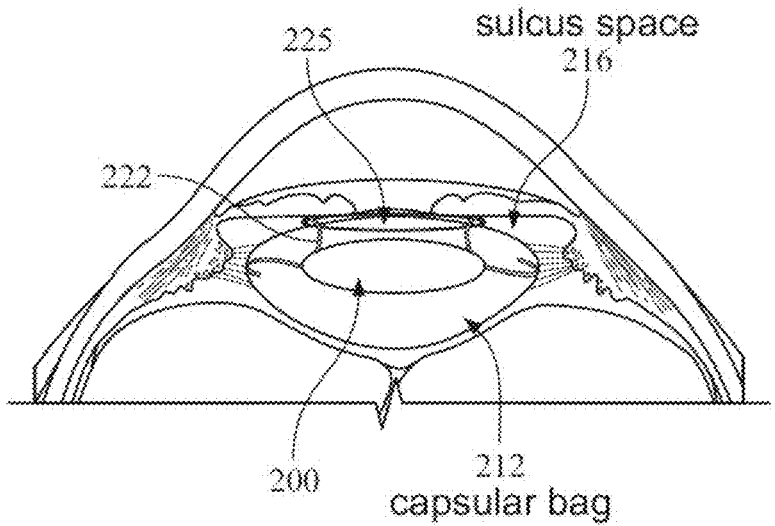
FIG. 2B illustrates extensions off of an exchangeable optics system that extend into a sulcus space through holes in the capsular bag.
Figure 2C:
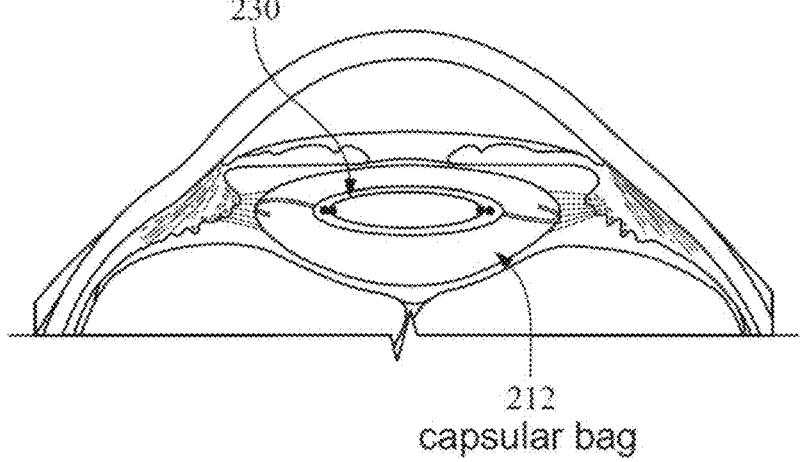
FIG. 2C illustrates an exchangeable optics system positioned entirely within the capsular bag.

FIGS. 2A-2E illustrate various locations in the eye where an exchangeable optics system can be set. FIGS. 2A-2C show examples of an intraocular base of an exchangeable optics system being positioned within a capsular bag of the eye. Referring to FIG. 2A, an intraocular base 200 of an exchangeable optics system 210 can be positioned within the capsular bag 212 of an eye. Through use of magnetic coupling, an exchangeable optic 215 (or therapeutic) can be deployed to (and even later removed from) the sulcus space 216 of the eye. Referring to FIG. 2B, an intraocular base 220 having extensions 222 can be positioned within the capsular bag 212 of an eye. The extensions 222 (or other protruding structure) can be extended into the sulcus space 216 through one or more holes in the capsular bag 212. For example, there may be an opening from cataract surgery through which the extensions 222 can protrude. In some cases, small openings may be made to allow for the extensions 222 to protrude through. Magnetic, mechanical, or chemical couplers may be provided at the end of the extensions 222 for an exchangeable optic 225 that is deployed to (and even later removed from) the sulcus space 216 to couple to. Referring to FIG. 2C, an exchangeable optics system 230 can be positioned entirely within the capsular bag 212.

Figure 2D:
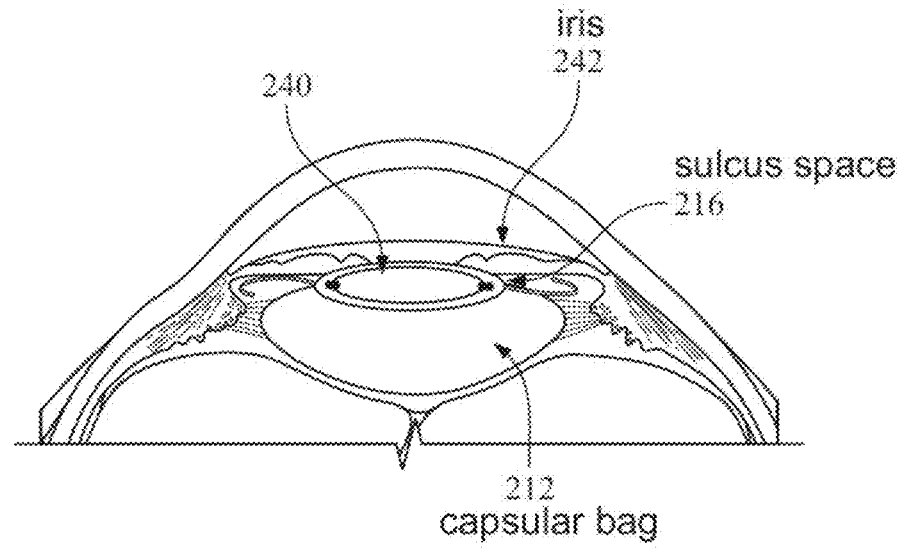
FIG. 2D illustrates an exchangeable optics system positioned entirely in the sulcus behind an iris.
Figure 2E:
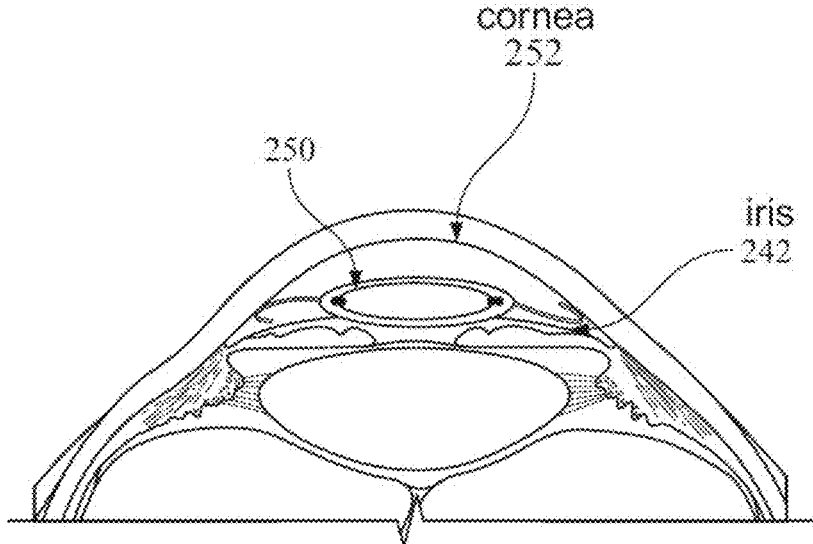
FIG. 2E illustrates an exchangeable optics system positioned in the anterior chamber behind the cornea, in front of the iris various locations in the eye where an exchangeable optics system can be set.

Referring to FIG. 2D, in some cases, an exchangeable optics system 240 can be positioned entirely in the sulcus 216 behind the iris 242, in front of the capsular bag 212. Referring to FIG. 2E, in some cases, an exchangeable optics system 250 can be positioned in the anterior chamber behind the cornea 252, in front of the iris 242. The examples shown in FIGS. 2D and 2E could work with a patient that is phakic (with native lens). Advantageously, if the intraocular base is fixed in the anterior chamber (such as shown in FIG. 2E) or in the sulcus space (such as shown in FIG. 2D), cataract surgery may not be required.

For any of these locations, if weight of the system is ever greater than zonular strength, an air bladder or portion of the device that floats in aqueous can be incorporated in the intraocular base. This buoyant component of the invention can be permanently incorporated, for example a compressible foam buoy that has sealed foam used in nautical equipment, pool toys and body boards. Alternatively, the device can have a reservoir that acts as a bladder that is filled with a gas or any material lighter than water. This would enable adjustable buoyancy based upon the degree of fill.

As mentioned above, the one or more couplers 110 (and corresponding one or more couplers 180) can include magnetic material or other releasable fixation material or structures. For example, the releasable couplers can be in the form of a hook and loop coupler, a memory material fixation element such as what is utilized for tagging guns for affixing tags to clothing, a button fastener, a screw-type fastener, a hinge-based fastener similar to a cuff link, a suction cup based mechanism, an adhesive, or any other means of reversible fixation.

Figure 4:
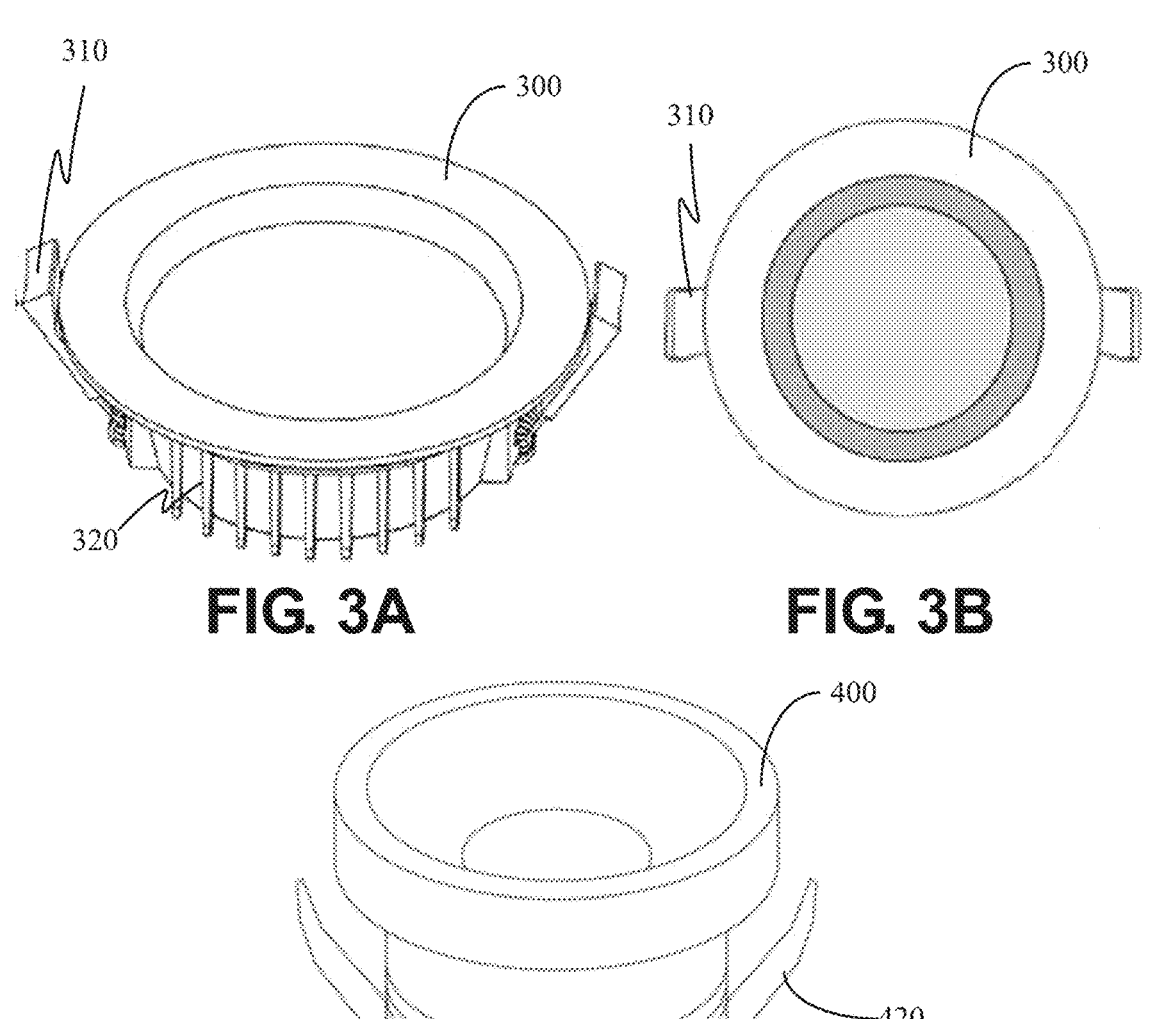
FIG. 4 illustrates a perspective view of an exchangeable optic with a screw mount for coupling to an intraocular base.

FIGS. 3A and 3B illustrate a perspective view and a top view, respectively, of an exchangeable optic with clips for coupling to an intraocular base; FIG. 4 illustrates a perspective view of an exchangeable optic with a screw mount for coupling to an intraocular base; and FIG. 5 illustrates a side view of part of an exchangeable optic system with a post and clip coupling.

Referring to FIGS. 3A and 3B, an exchangeable optic 300 can have a clip 310 that can attach to a coupler of an intraocular base (not shown). In some cases, the exchangeable optic 300 can include ribs 320 to assist with a secure fit, for example, within a main structure of the intraocular base.

Referring to FIG. 4, an exchangeable optic 400 can have a screw mount 410 for securing to a corresponding coupler at an intraocular base (not shown). In some cases, the exchangeable optic 400 can include prongs 420 to assist with a secure fit, for example, within a coupler and main structure of the intraocular base.

Figure 5:
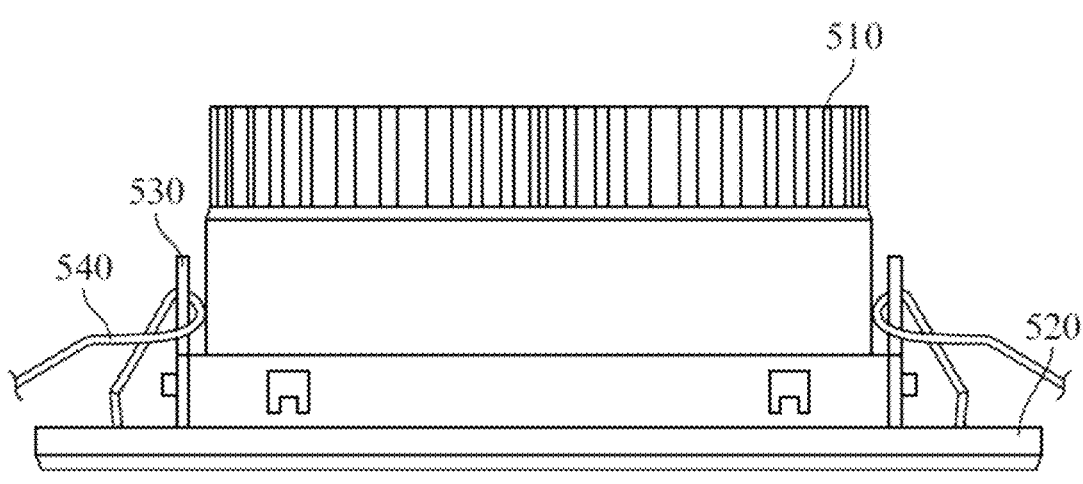
FIG. 5 illustrates a side view of part of an exchangeable optic system with a post and clip coupling.

Referring to FIG. 5, an exchangeable optic 510 can be coupled to an intraocular base 520 using a post 530 and nitinol clip 540.

For any direct connection between a base and an exchangeable optic (or between two exchangeable optics), it is desirable that the coupling mechanism is located within the confines of the anterior rhexis. This will enable direct connection between the exchangeable optic (e.g., exchangeable optic 225 of FIG. 2B) outside of the capsular bag 212 and the intraocular base (e.g., intraocular base 220 of FIG. 2B) in the capsular bag. Alternatively, femtosecond laser or other precision surgical platform can not only make the primary rhexis but also make two or more small secondary opening in the anterior capsule through which a coupling mechanism (e.g., extensions 222) can protrude. The use of the femtosecond laser or other precision surgical platform to form secondary openings through which a coupling mechanism can protrude may serve a secondary function of aligning a lens in a particular axis, which is useful, for example, with toric IOLs. Indeed, the femtosecond laser or other precision surgical platform can be used to make two additional holes adjacent to the rhexis at the axis the IOL must be through.

There are numerous coupling mechanisms that may be used instead of or in addition to magnetic material. In some cases, the exchangeable optic can have a fixation element that has a shape memory material component that can be placed through a hole at the intraocular base through the holes made in the anterior capsule. Similar to a tagging gun used to attach price tags to clothing, the T arms can flex when being pushed through the hole in the optic haptic junction and return to an open position once through the hole.

As is clear to one skilled in the art, this arrangement can be modified in numerous ways. For example, in some cases, the T arm fixation element can be incorporated into the intraocular base and project through the capsular bag into the sulcus space. The exchangeable optic can have a hole in it through which the T fixation element projects. This may be a preferable option if capsular bag phimosis causes the capsular bag to shift in position in relation to the hole in the primary optic. By having the T fixation element project beyond the capsular bag, this helps ensure maintained access to the coupling mechanism, even if capsular phimosis occurs. In addition, the T-shape fixation element can be made of a variety of memory materials including shape memory polymers and shape memory metals. Suitable memory polymers for the described fixation elements include, but are not limited to, polynorbomene, polycaprolactone, polyenes, nylons, polycyclooctene (PCO), blends of PCO and styrene-butadiene rubber, polyvinyl acetate/polyvinylidinefluoride (PVAc/PVDF), blends of PVAc/PVDF/polymethylmethacrylate (PMMA), polyurethanes, styrene-butadiene copolymers, polyethylene, trans-isoprene, blends of polycaprolactone and n-butylacrylate, and combinations thereof. Suitable memory metals for the described fixation elements include, but are not limited to, stainless steel, cobalt, nickel, chromium, molybdenum titanium, nitinol, tantalum, platinum-iridium alloy, gold, magnesium, or combinations thereof. Further, it should be understood that other end shapes may be used for the T shape fixation element. For example, the end shape may be a circle, triangle or any shape that is larger than the hole it is to be fixated through.

In some cases, the intraocular base or the exchangeable optic can have posts that project either through the anterior capsulotomy or through the secondary holes created in the anterior capsule. In one such implementation with a post projection, an exchangeable optic could then fit through the posts and an elastic band can be placed over the exchangeable optic onto the post thereby holding the exchangeable optic in place. The elastic band that retains the exchangeable optic can operate similar to how rubber bands hold a wire in place to the bracket on dental braces. In another implementation of a post projection, the post could have a thread on it in which a screw can mount. In another implementation, the post can include a hole through which a cotter pin or memory material can be placed through. In another implementation, the post can include a lever arm. Similar to a cuff link, the post can either be straight up and down or when turned at the hinge will form a T. This arrangement does not involve shape memory but instead just a mechanical hinge. An exchangeable optic with a feature similar to a shirt cuff can be threaded over the fixation element when it is in a straight position and then once in place the hinge can be turned so instead of straight the post forms a T thereby holding the exchangeable optic and the intraocular base together.

In some cases, the intraocular base and the exchangeable optic can use a snap-button arrangement, for example, if designed with low enough friction.

In some cases, the intraocular base and the exchangeable optic can use a twist on mechanism in conjunction with posts, where the posts include a T or L shaped end and once the posts pass through the opening in the other part, the exchangeable optic can be rotated so that the end of each post catches on a surface to hold the two in place. For example, if one post element is in the shape of a L but the slot it passes through only is slightly larger than the horizontal component of the L, then if the intraocular base and the exchangeable optic are rotated in relation to each other, the leading edge of the L moves beyond the edge of the slot it passes through thereby holding the intraocular based and the exchangeable optic together. In some cases, a shape memory material can be incorporated. For example, the L shape can have a projection at the very end (such as in the form of a very pronounced serif L). The projection at the end of the L can fit into a hole that is adjacent to the notch (e.g., similar to that employed in some ballpoint pens). Thus, as the L shape is threaded through the notch, the projection portion at the end of the L abuts the edge of the notch and is bent slightly out of the way so rotation can continue. Once rotated far enough that the projection on the L reaches the hole next to the notch and falls into place thereby enabling the L to again be coplanar with the intraocular base and exchangeable optic. In some cases, both the exchangeable optic and the L shaped post can be formed of materials with memory shape properties FIGS. 6A-6D illustrate an exchangeable optics system with multiple stacked lenses. FIG. 6A illustrates an exploded view of an exchangeable optics system 600 that includes an intraocular base 610 and a plurality of optics (including first optic 621 and second optic 622). The intraocular base 610 can have a supporting structure 630 with a haptic ring 640 that can be sutured for fixed connection to an eye. One or more couplers can be on the supporting structure. For example, the one or more couplers can be point sources or a ring (such as represented by white dotted line 650) that is disposed on or goes around a circumference of the supporting structure (see also e.g., FIGS. 11A and 11B). Referring to FIG. 6B, the intraocular base 610 can be disposed in the eye (e.g., in the sulcus space). As shown in FIG. 6C, the first optic 621 can be releasably attached to the intraocular base 610. Alternatively, in some cases, the first optic 621 (or a third optic) is fixedly attached to the intraocular base 610 or is built-in to the intraocular base (see e.g., lens 1060 of FIG. 10). Then, as shown in FIG. 6D, the second optic 622 can be releasably attached to the intraocular base 610 over the first optic 621. In some cases, the magnetic force from the intraocular base 610 is sufficient to couple both optics. In some cases, the positioning of the two optics enable at least a portion of the one or more couplers to be dedicated to a respective one of the two (or more) optics. In some cases, the first optic 621 includes one or more couplers for the second optic 622 to couple to. In some cases, the first optic 621 is fixedly attached to the intraocular base 610 and the couplers on the supporting structure are configured for attachment of the second optic 622.

Figure 7B:
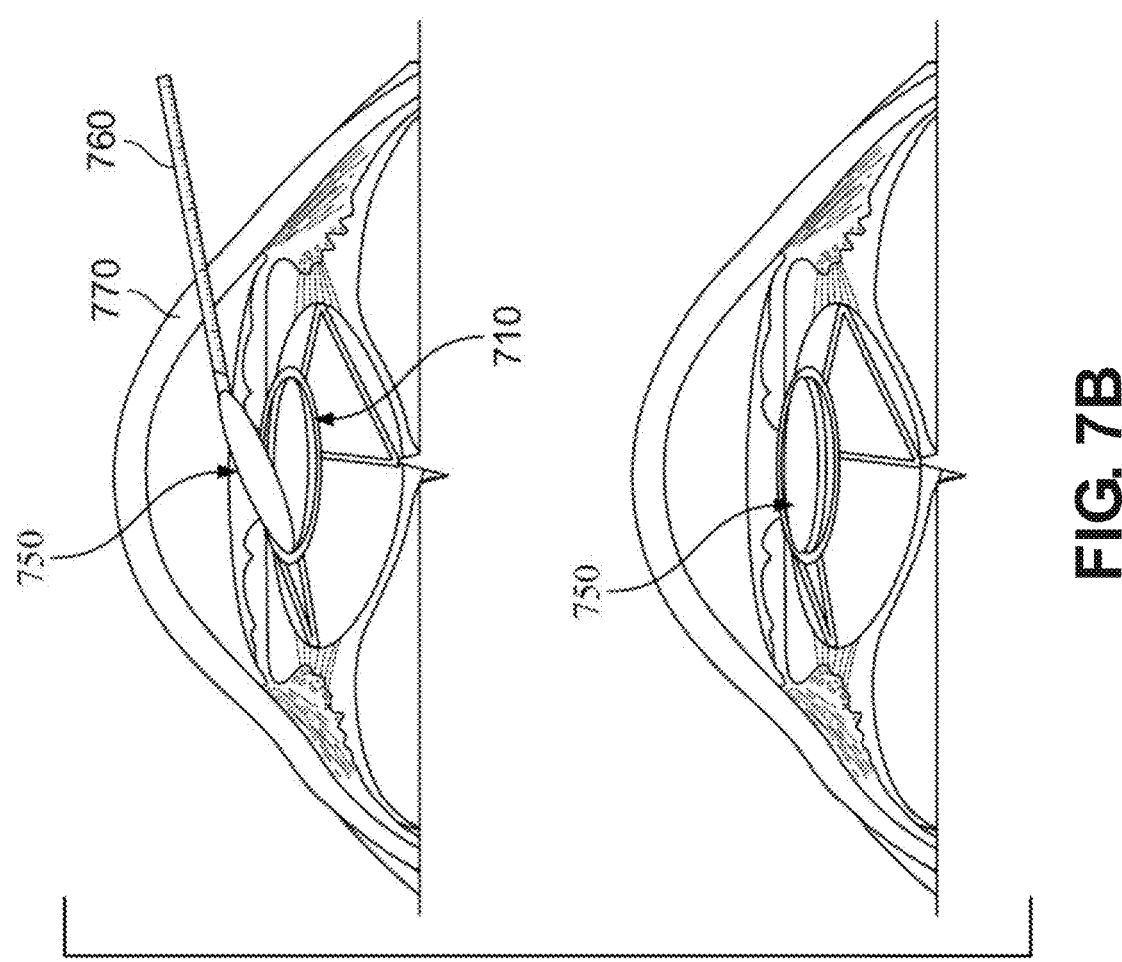
FIG. 7B illustrates the intraocular base of FIG. 7A to which a second optic is applied onto the intraocular base and first optic using a delivery system.
Figure 7A:
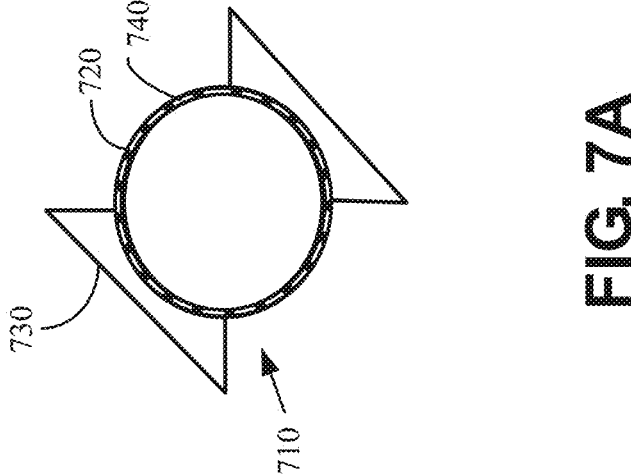
FIG. 7A illustrates another example of an intraocular base.

FIGS. 7A and 7B illustrate another exchangeable optics system with multiple stacked lenses; FIG. 7A shows another example of an intraocular base; and FIG. 7B shows application of a second optic onto the intraocular base and first optic using a delivery system.

Referring to FIG. 7A, an intraocular base 710 can have a supporting structure 720 with a haptic 730 that can be sutured for fixed connection to an eye. One or more couplers can be on the supporting structure 720. For example, the one or more couplers can be point sources or a ring (such as represented by white dotted line 740) that is disposed on or goes around a circumference of the supporting structure (see also e.g., FIGS. 11A and 11B).

Turning to FIG. 7B, a lens 750 can be easily applied to the intraocular base 710 via a tool (optic delivery system 760) through a small incision in the sclera 770. An optic delivery system 760 can include a hook or other fine instrument that can be drawn coaxially, allowing for a minimal incision that minimizes changes to corneal astigmatism and damage to the ocular structures after optic introduction or exchange. The optic delivery system can coaxially store a capsular bag containing a new optic containing, for example, the secondary lens 750 and enter through a minimal incision. As shown in FIG. 7B, once inside the eye close to the location of the intraocular base 710, the optic delivery system 760 can release the capsular bag close into the sulcus space. The hook (see FIG. 8) can be used to maneuver the capsular bag or secondary lens to be oriented properly with respect to the intraocular base 710. At some point, the new optic 750 can couple to the intraocular base, at which point the hook can optionally be used to properly orient the new optic with respect to the intraocular base. Fiducial markers may be used to facilitate orientation and alignment (see e.g., FIGS. 9A and 9B, which can be used under optical coherence tomography—OCT) In some cases, the exchangeable optics (e.g., lens 750) can include an aperture, which may be hooked by the instrument of the optic delivery system.

In this illustrated scenario, the lens 750 is a second optic; however, this method can be carried out for the first optic (e.g., optic 621) and even a replacement second optic (e.g., to replace the second optic 622 after optic 622 is applied as shown in FIG. 6D).

Figure 8:
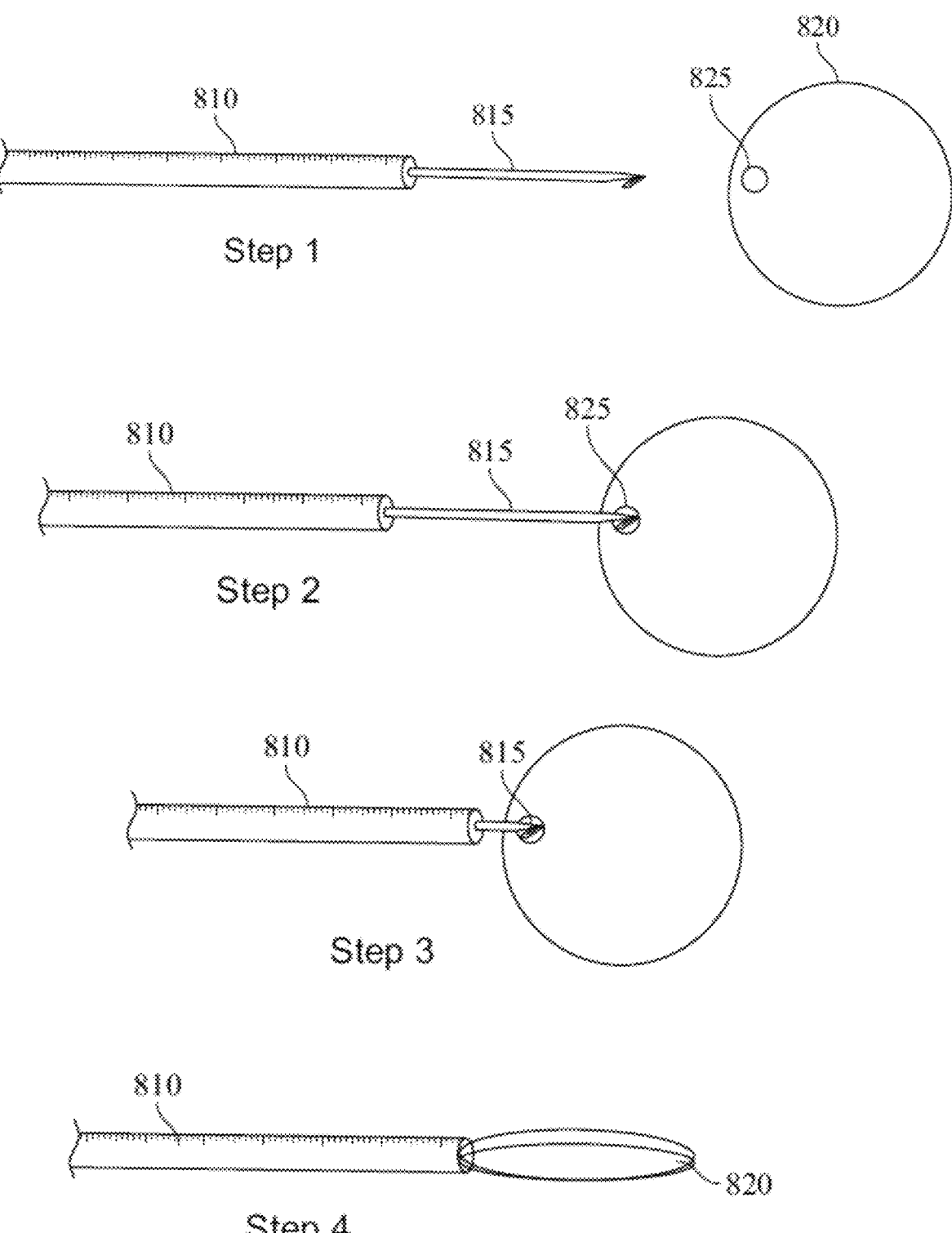
FIG. 8 illustrates an optic delivery system consisting of a hook that can be drawn coaxially within a delivery sleeve.

FIG. 8 illustrates operation of an optic delivery system. Referring to FIG. 8, an optic delivery system 810 can include a hook 815, which can be drawn coaxially into the eye within a delivery sleeve of the optic delivery system 810. In a first step, the hook 815 can be in the extended position. As illustrated in a second step, the hook 815 can engage a hole 825 within the periphery of the optic 820 to enable extraction. As illustrated in the third step, the hook 815 can then be drawn coaxially back into the optic delivery system 810, bringing the optic 820 towards the delivery sleeve. At a certain point, the hook 815 can be drawn entirely within the optic delivery system 810, at which point the optic 820 can be forced to fold inwards and be drawn with the hook into the optic delivery system 810, such as shown in step 4.

FIGS. 9A and 9B show fiducial designs that can enable precise orientation of three-dimensional rotation of an optic or haptic. Fiducials can be placed, etched, or drawn onto a lens or other optic to aid in orientation of the lens or other optic once deployed. The fiducial markers can be of a material suitable for detection by IR, ultrasound, fluorescent, x-ray, MRI, etc. In one implementation, the fiducials can be detectable by an ocular response analyzer (e.g., optical coherence tomography—OCT). The fiducial markers can be used to determine precise effective lens position (ELP). Corresponding markers can be applied to an intraocular base at haptics, on the optional lens, or on the supporting structure, as some examples. In some cases, a corresponding fiducial design may be disposed at the intraocular base (e.g., on main structure region 160 of FIG. 1A).

Referring to FIG. 9A, the fiducial can be L-shaped. Arms of the L shape can vary. If the size and shape of the L-shaped fiducial is known, apparent length can be used to inform rotation of the lens or optic in three dimensions. Referring to FIG. 9B, the fiducial can be bulls-eye-shaped (e.g., a single dot within a circle). In particular, use of a bulls-eye shape can allow part of the fiducial to be printed on an opposite side of the lens or optic. The fiducial being on both sides of the lens or optic can create greater apparent motion of the dot relative to the circle, allowing a more accurate understanding of its orientation in three-dimensional space.

A few L shaped fiducials printed on one side of the lens or haptic receiving system (e.g., as shown in FIG. 9A) or a circle on one side of the lens and a dot on the other placed within the circle when viewed anterior/posterior (e.g., providing a bullseye such as shown in FIG. 9B) will enable a sensitive measurement of any tilt. By visualizing the length of the L arms or where the dot is in relation to the circle it is possible to determine where the lens or haptic receiver is located.

In some implementations, fiducials are provided on both the exchangeable optic and the intraocular base that can be read using OCT. The fiducials can be read in relation to a stationary feature of the eye (e.g., conjunctival vessel pattern preregistered with corneal topography/tomography, biometry data, etc.). The OCT can then guide placement of the optic on haptic. The fiducials support real time tracking of the intraocular base in case the intraocular base moves when the exchangeable optic is removed. When the exchangeable optic is repositioned or replaced, the OCT device can calculate in real time with the fiducials what position change is necessary.

As mentioned above, an exchangeable optics system can include a variety of structures for the intraocular base. In addition, the couplers of the intraocular base can be disposed in various locations and be configured in various shapes. The following examples are directed to exchangeable optics systems with intraocular bases having magnetic coupling; however, embodiments are not limited thereto.

Figure 10:
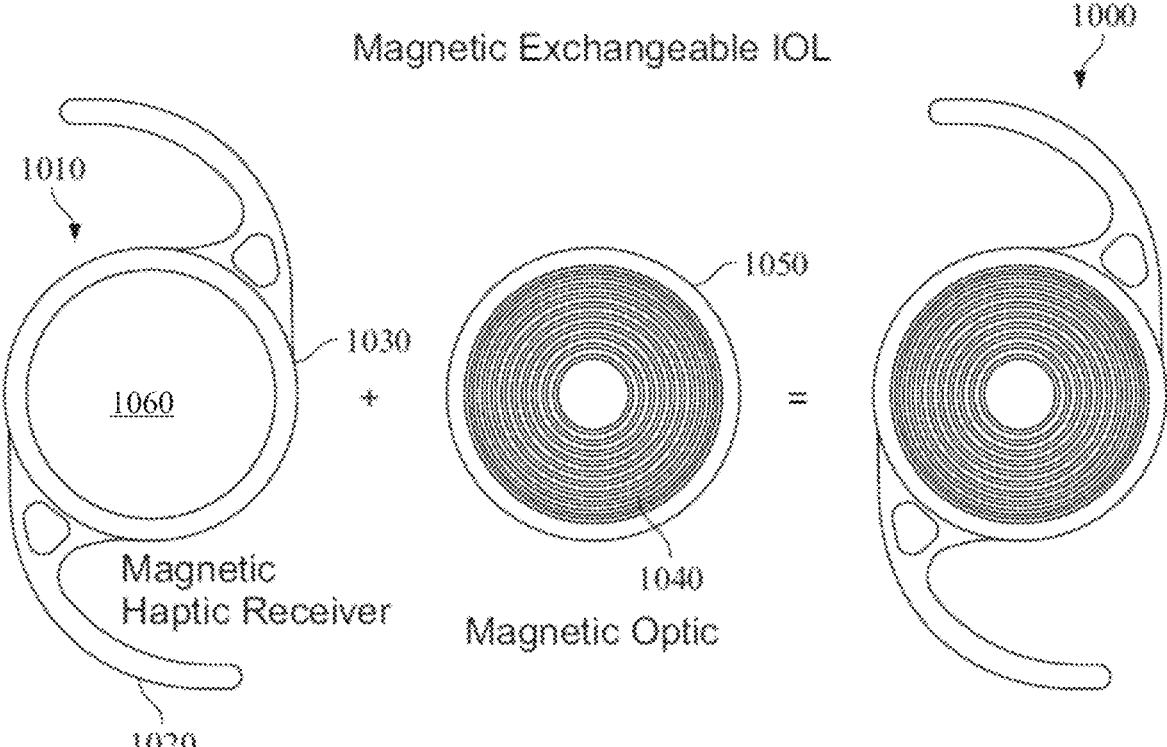
FIG. 10 illustrates an example exchangeable optics system with magnetic exchangeable intraocular lens.

FIG. 10 illustrates an example exchangeable optics system with magnetic exchangeable intraocular lens. Referring to FIG. 10, an exchangeable optics system 1000 can include an intraocular base 1010 with haptics 1020 and a circular magnet coupler 1030; and an exchangeable optic 1040. The exchangeable optic 1040 can be a magnetic optic with a corresponding circular magnet 1050 around its periphery.

In the illustrated scenario, the haptics 1020 are in the form of a two C-loop haptic. In some cases, the intraocular base 1010 can further include a lens 1060. For example, the intraocular base 1010 can be similar to a conventional IOL, but further includes the one or more couplers (e.g., here in the form of a magnet disposed at a periphery). A magnetic optic 1040 can then be deployed, rotated to any precise orientation, for example aligned using fiducials such as shown in FIGS. 9A and 9B, and coupled to the intraocular base structure 1010. In some cases, the exchangeable optic 1040 may not be deployed for potentially years down the line and/or may be replaced years later to deploy a more precise lens. An intraocular base structure 1010 that allows for deployment, rotation, and coupling of a magnetic optic (e.g., exchangeable optic 1040) can be advantageous, for example, in precise toric astigmatism correction. In addition, since it is possible to add additional lenses and/or replace the exchangeable optic 1040, it is possible to add a further corrective lens after a more disruptive surgery, add a corrective lens years after the fact, or deploy a more precise lens, for example a specially made or three-dimensional printed lens.

Figures 11A, 11B, 11C, 11D:
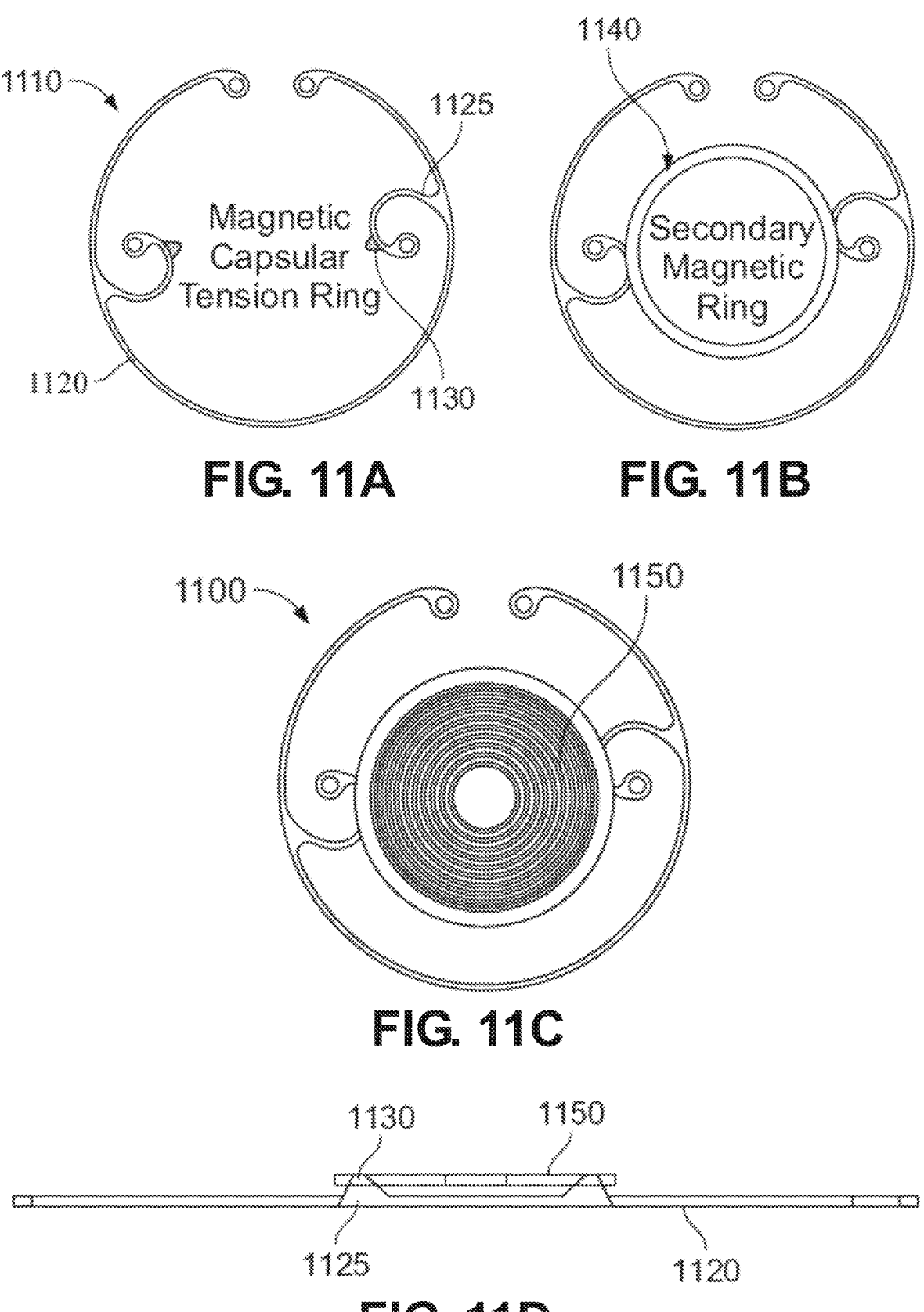
FIG. 11A illustrates a magnetic capsular tension ring (CTR) with tension ring extensions in accordance with an embodiment.
FIG. 11B illustrates the magnetic capsular tension ring of FIG. 11A onto which a secondary magnetic ring is attached.
FIG. 11C illustrates magnetic optics coupled to the magnetic capsular tension ring of FIG. 11B.
FIG. 11D is a side view of the assembly of FIG. 11C.

FIGS. 11A-11D illustrate another example of an exchangeable optics system with magnetic exchangeable ocular lens. Referring to FIGS. 11A and 11D, in exchangeable optics system 1100, an intraocular base 1110 can include a capsular tension ring 1120 with optional tension ring extensions 1125 and two or more couplers 1130. As mentioned above with respect to FIG. 2B, through use of one or more protrusions such as tensions ring extensions 1125, the capsular tension ring 1120 can be designed in such a way that two or more magnetic arms (e.g., tension ring extensions 1125 with couplers 1130) emerge through the anterior capsulotomy similar to an Ahmed segment thereby enabling optic placement in the sulcus space. Alternatively, the capsular tension ring can be designed such that the capsular tension ring does not rise up out of the anterior capsulotomy but instead remains in bag. In some cases, in addition to the couplers 1130 or as an alternative to the couplers 1130, a secondary magnet ring 1140 can be included, which can provide a 360-degree docking platform for magnetic optics 1150, as shown in FIGS. 11C and 11D. That is, as shown in FIG. 11C, an optic with corresponding couplers can be deployed, and attraction between the couplers 1130 on the arms of the capsular tension ring 1120 (and/or optionally the secondary magnet ring 1140) and the corresponding couplers on the optic 1150 can releasably maintain the optic 1150 in place. As mentioned with respect to FIG. 1A, in some cases, a primary lens can be provided as part of the intraocular base 1110 (e.g., within the secondary magnetic ring 1140 shown in FIG. 11B). In some cases, the magnetic optic 1150 can be deployed, rotated to a precise orientation, for example aligned using fiducials such as shown in FIGS. 9A and 9B, and coupled to the intraocular base structure 1110 on the secondary magnet ring 1140.

Figure 12A:
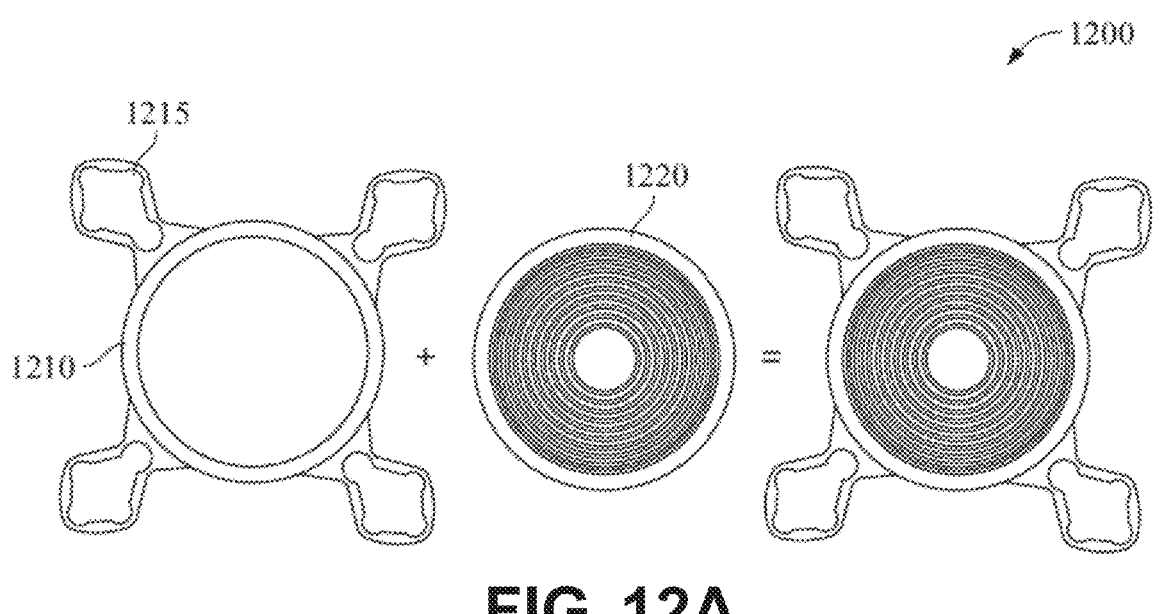
FIG. 12A illustrates an exchangeable optics system with a cruciate haptic pattern and magnetic coupling optic.
Figure 12B:
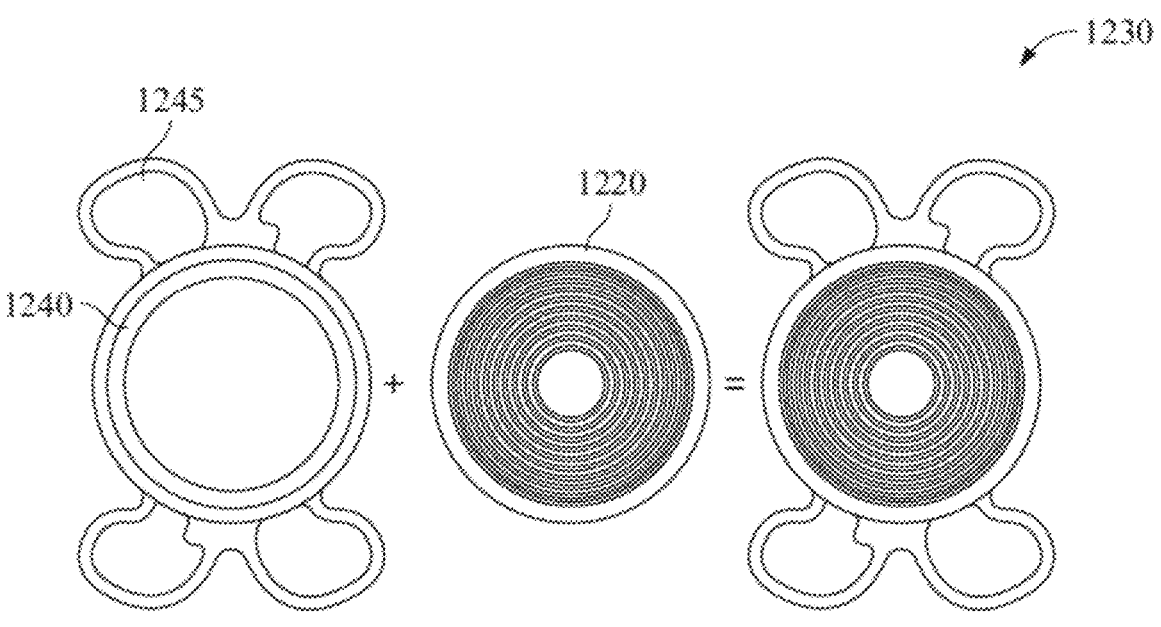
FIG. 12B illustrates an exchangeable optics system having a haptic design that can facilitate a secondar scleral sutured lens.
Figure 12C:
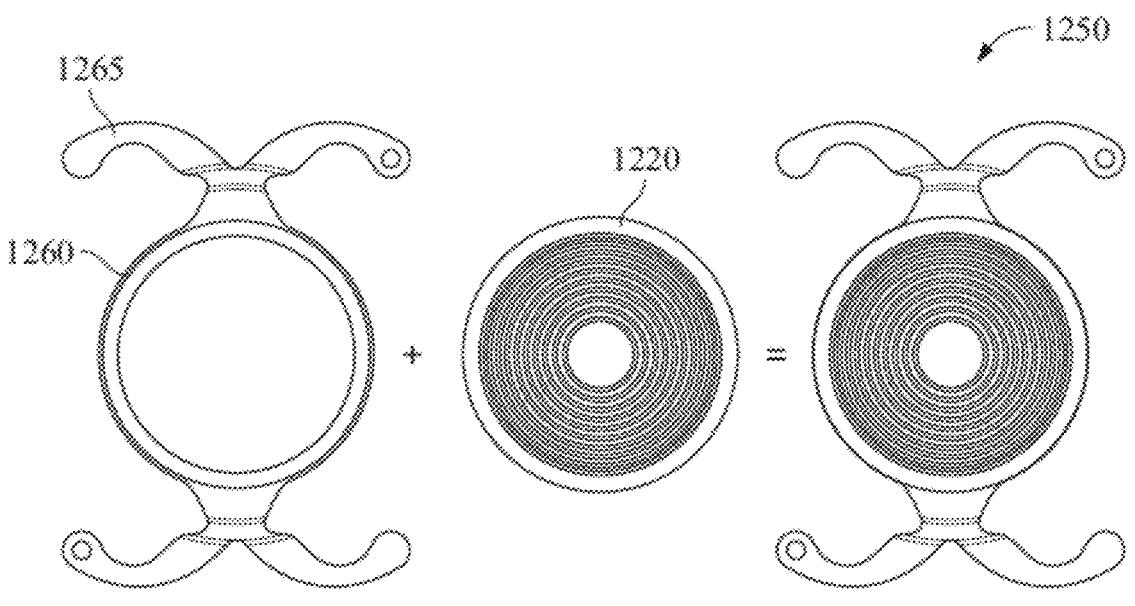
FIG. 12C illustrates an exchangeable optics system with an intraocular base design having a four-pronged haptic arm and magnetic coupling optic.
Figure 12D:
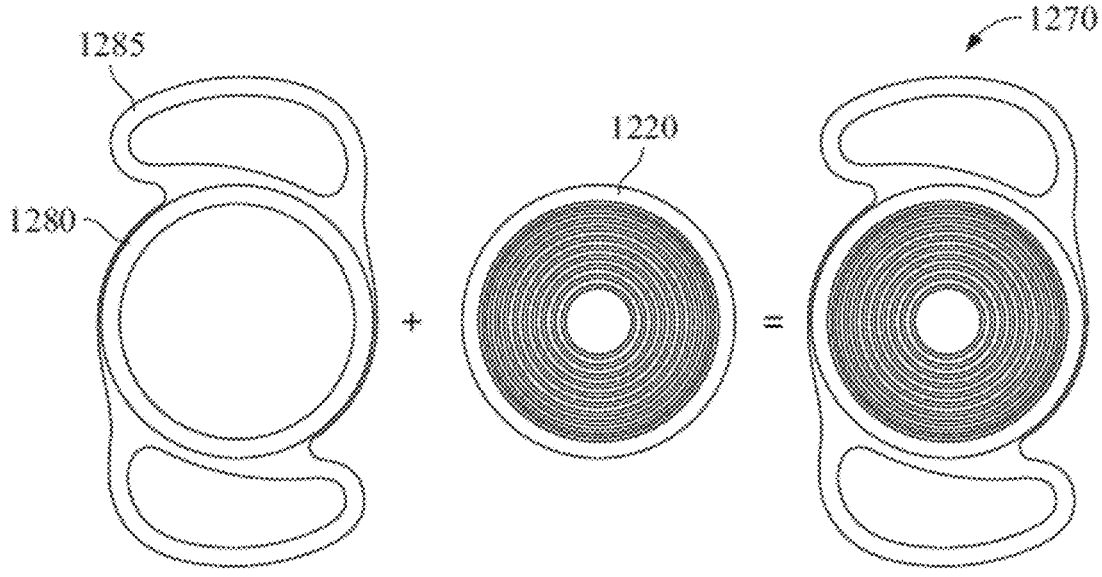
FIG. 12D illustrates an exchangeable optics system with an intraocular base design having a looped haptic and magnetic coupling optic.

FIGS. 12A-12D illustrate example haptic designs for exchangeable optics systems. A supporting structure of an intraocular base can be implemented with haptics of a variety of different shapes and patterns. In addition to the shapes shown in FIGS. 6A and 7A, the two-looped C shaped haptic such as shown in FIG. 10 and the capsular tension ring configuration shown in FIG. 11A, other haptic shapes may be used. For example, FIG. 12A shows an exchangeable optics system 1200 with an intraocular base 1210 design having a cruciate haptic pattern 1215 and a magnetic coupling optic 1220. FIG. 12B shows an exchangeable optics system 1230 with an intraocular base 1240 design having a haptic design 1245 that can facilitate secondary scleral sutured lens similar to the Gore Akreos lens and a magnetic coupling optic 1220. FIG. 12C shows an exchangeable optics system 1250 with an intraocular base 1260 design with four-pronged haptic arm 1265 and a magnetic coupling optic 1220. FIG. 12D shows an exchangeable optics system 1270 with an intraocular base 1280 design with looped haptic 1285 and a magnetic coupling optic 1220.

With cataract surgery, the shape of the corneal as well as the optics of the lens and the effective lens position are altered. Even if precisely positioned in the appropriate location, postoperative shifting of the lens is not uncommon. An exchangeable optics system such as described herein can address these obstacles. First, by sandwiching the capsular bag between the magnetic optic and magnetic haptic receiver through the bag, the system is less likely to rotate or shift in relation to the capsular bag. Second, in certain embodiments, such as 3D printing of a wavefront guided or ray traced custom intraocular lens, it may make more sense to allow an intraocular base with a lens haptic system to scar into the capsular bag. As the capsule contracts, the final effective lens position of the intraocular base will then be known. By including fiducials, a wavefront or ray traced scan can calculate shape of cornea after cataract surgery, an effective lens position can be determined from fiducials, and this data can be used to 3D print a custom lens when all variables are achieved. The custom lens can then be attached afterwards to the determined specifications. This would enable the ability to not only print wavefront/ray trace optimized monofocal IOLs, but also custom wavefront optimized/ray traced multifocal and extended depth of focus intraocular lens. An intraocular base also provides a forward compatible system for any future iteration of lens since the lens can be replaced/exchanged with the newest iteration of the lens.

In some of such cases, the lens providing the primary power can be deployed with the intraocular base (see e.g., lens 1060 described with respect to FIG. 10) and a wavefront guided/ray traced optic can be delivered secondarily for attachment to the intraocular base that has the lens 1060. The wavefront guided/ray traced optic ("second lens") can be deployed through a far smaller incision and similar to ICL surgery and LASIK, may be amenable to office-based procedures. That is, the secondary optic can be deployed through a small enough corneal incision or previous surgical incisions can be accessed, and the additional variability created by reentering cornea can be minimized. This would enable the primary lens and haptic system to be deployed in the bag similar to current IOLs, just with a magnetic system. At a secondary time period in which the capsular bag has fully contracted, the fiducials provide effective lens position. In addition, by using topography/tomography and wavefront/ray traced measurements of the length of the eye, all the optical variables could be controlled for. If necessary, the degree of astigmatism induced by penetrating the cornea to deliver the secondary optic can be controlled for with custom optic design adjusted to account for the induced astigmatism. Thus, it is possible to a priori determine effective lens position (ELP) and determine what custom or non-custom lens would be ideal for an eye.

Figure 13A:
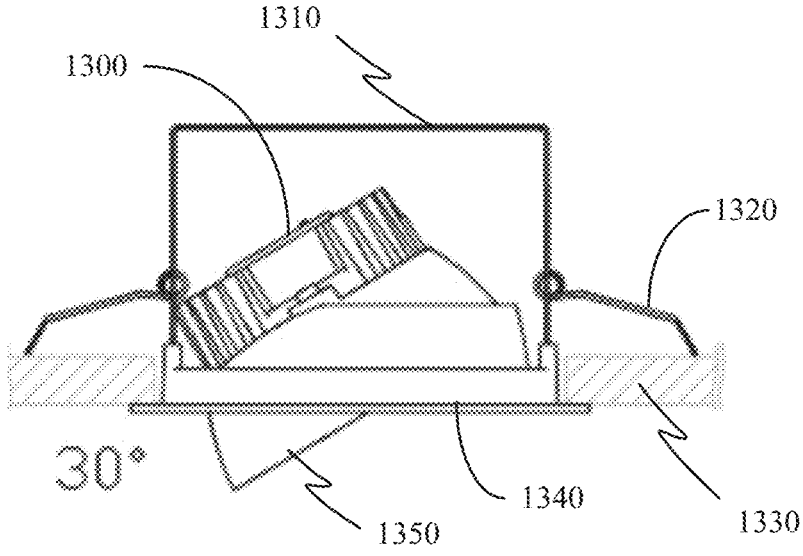
FIG. 13A is a side view of an exchangeable optic with rotatable lens.
Figure 13B:
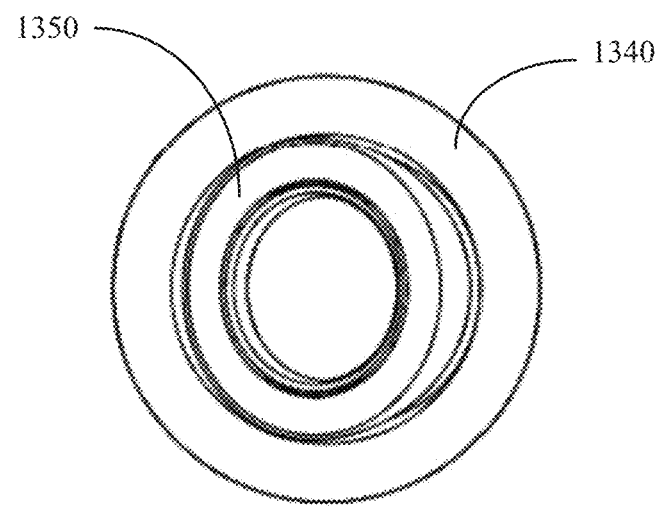
FIG. 13B is a top view of the exchangeable optic with rotatable lens of FIG. 13A.

Specialized optics can be applied to an intraocular base as part of the described exchangeable optics systems. FIGS. 13A and 13B illustrate a side view and top view, respectively, of an exchangeable optic with rotatable lens. A lens housing system is provided for a rotational design that enables rotation of a lens of intraocular base or an exchangeable optic. Referring to FIG. 13A, a design for an exchangeable optic 1300 can have a coupling frame 1310 to which couplers 1320 of an intraocular base 1330 can be attached; a stationary body 1340 that can fit within an opening of the intraocular base 1330 and a rotating body 1350 which can rotate in one or two dimensions, depending on coupling between the stationary body 1340 and the rotating body 1350.

Figure 14A:
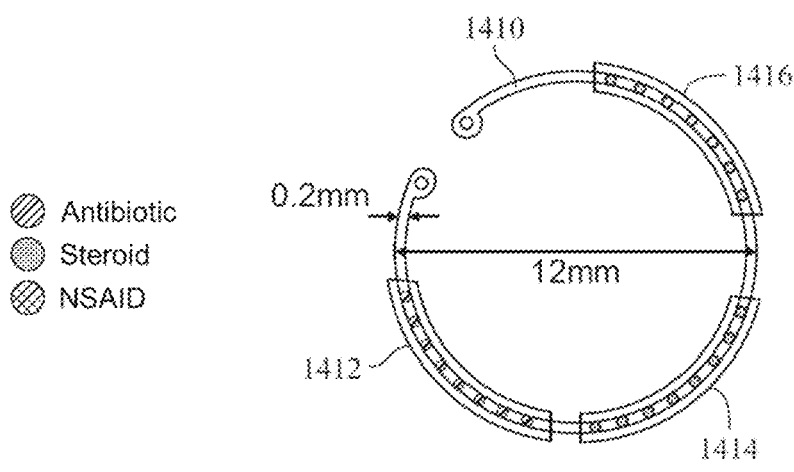
FIG. 14A illustrates a capsular tension ring coated with magnetic material that attracts magnetic particles for therapeutic delivery.
Figure 14B:
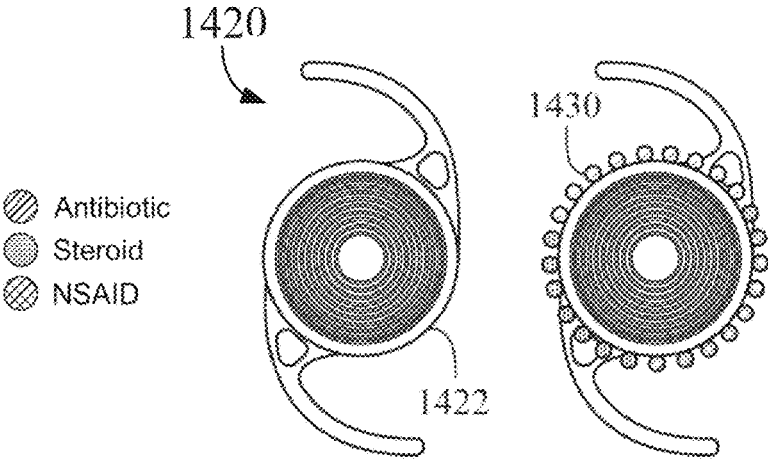
FIG. 14B illustrates an intraocular base having a magnetic coupler/ring used to attach magnetic particles for therapeutic delivery.
Figure 14C:
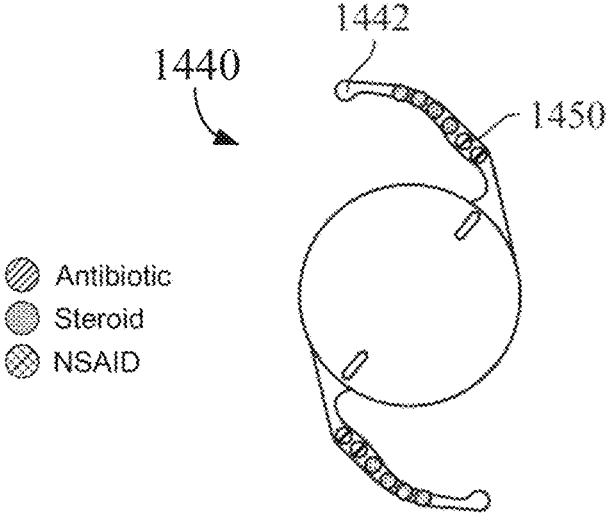
FIG. 14C illustrates an intraocular base with magnetic haptics used to attach magnetic particles for therapeutic delivery.

As previously mentioned, an intraocular base can be used not just to support delivery of exchangeable optics, but also to provide a surface for delivery of therapeutics. FIGS. 14A-14C an example of an exchangeable optics system with therapeutic delivery.

Magnetic liposomes or nanoparticles can be used in conjunction with magnetic components of an exchangeable optics system.

In addition to incorporating drug delivery polymeric implants or reservoirs directly into the haptic or optic system of the device, the magnetic components of the intraocular base provide a means of coupling magnetic nanoparticles and liposomes to the device. The magnetic liposomes or particles may be preloaded onto the device and administered at the time of surgery or after surgery.

Figure 15A:
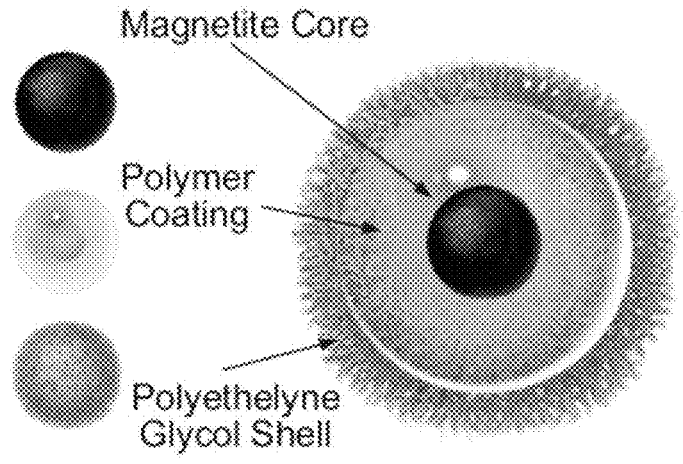
FIG. 15A illustrates a magnetic particle formed of a magnetite core with a polymer coating and polyethylene glycol shell that can be used for delivery of therapeutics on an exchangeable optics system.
Figure 15B:
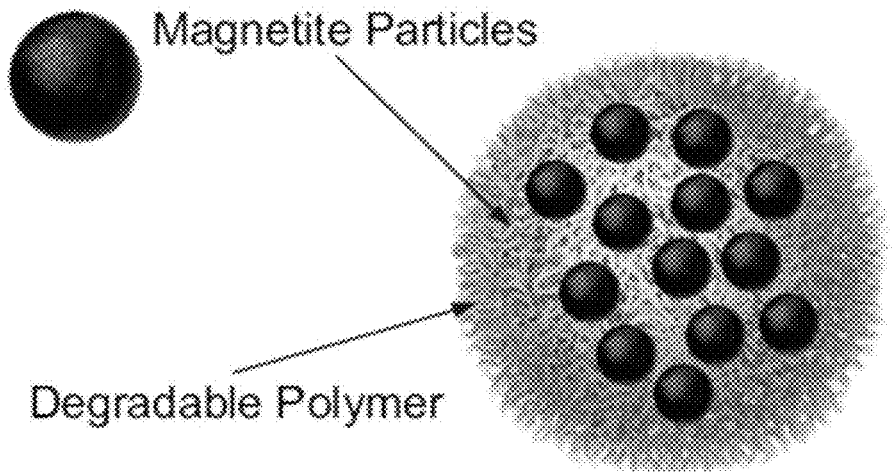
FIG. 15B illustrates a magnetic particle having a plurality of magnetic particles within a single polymer particle.
Figure 15C:
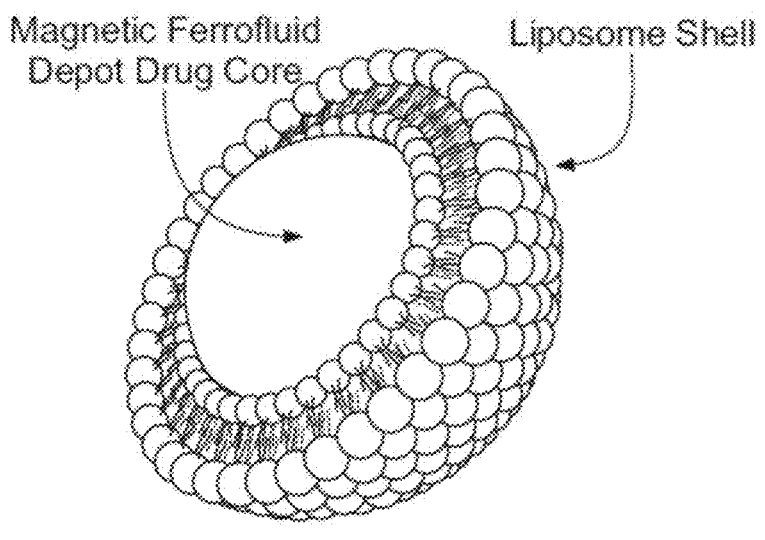
FIG. 15C illustrates a magnetic particle formed as a liposome particle with a ferrofluid core.

Magnetic liposomes or nanoparticles can be coupled to a magnetic intraocular base prior to deployment in the eye. Alternatively, or in addition, liposomes or nanoparticles can be introduced through an intravitreal, transzonular, intracapsular or intracameral approach after deployment of a magnetic intraocular base into the eye and be coupled to the magnetic intraocular base in the eye. The magnetic particles can be used to deliver therapeutics including, but not limited to antibiotics, steroids, and non-steroidal anti-inflammatory drugs (NSAIDs). These therapeutics can be configured such as illustrated in FIGS. 15A-15C to facilitate attachment to an intraocular base. Instead of rapidly exiting the eye through the normal outflow pathways, a magnetic intraocular base would enable the magnetic particles to dwell on the haptic system until they degraded or release ferrofluid to the point that the magnetic attraction is no longer sufficient to remain bound.

As mentioned above, the magnetic particles used to deliver the therapeutics can be applied to various forms of an intraocular base. Referring to FIG. 14A, an intraocular base 1410 in the form of a capsular tension ring can be formed of or coated with magnetic material that attracts the magnetic particles. In some cases, different regions can be applied with different therapeutics, for example, a region for antibiotics 1412, a region for steroid 1414, and a region for NSAID 1416. Of course, the therapeutics may be applied in a manner that the various therapeutics are disbursed throughout the surface of the intraocular base 1410.

Referring to FIG. 14B, an intraocular base 1420, with or without a lens, can include a magnetic coupler/ring 1422 that is used to attach magnetic particles 1430. The magnetic particles 1430 can thus be deployed and attached around the ring 1422.

Referring to FIG. 14C, an intraocular base 1440 with magnetic haptics 1442 can be used to attach magnetic particles 1450.

Referring to FIG. 15A, a magnetic particle can be formed of a magnetite core with polymer coating and polyethylene glycol shell. The magnetite cores can cause the magnetic particle to be attracted to the magnetic intraocular base allowing for relatively fine deployment. If a plurality of magnetite particles is present, attraction between the magnetic particle and the magnetic intraocular base is reduced. The strength of the magnetic on the magnetic intraocular base as well as the concentration of the magnetite, size of polymer particle, and rate of degradation can adjust the dwell time to further finetune localized dosage. In a particular embodiment, rate of polymer degradation can be tuned to drug release rate. This can allow the magnetic particle to disassociate after the majority—or even all of—the drug is delivered due to a decreased attraction.

Referring to FIG. 15B, a magnetic particle can have a plurality of magnetic particles within a single polymer particle instead of a single magnetite core as shown in FIG. 15A.

Referring to FIG. 15C, a magnetic particle can be formed as a liposome particle with a ferrofluid core. A therapeutic can include a liposome shell, a magnetic ferrofluid within the liposome shell, and a drug or therapeutic core within the liposome shell. The magnetic ferrofluid and drug or therapeutic core can be combined inside the liposome shell. Since the ferrofluid and therapeutics are combined within the liposome shell, release of the drug or therapeutic can coincide with release of the ferrofluid. In certain implementations, rate of ferrofluid release can be tuned to drug release rate so when the majority of drug is released the degree of attraction between the liposome and intraocular base is reduced to the point at which the liposome dissociates and then can freely flow through the trabecular meshwork out of the eye.

Since free iron is known to be toxic to the retina, magnetic nanoparticles are contained within a biocompatible shell much like current iron-based MRI contrast agents such as Ferridex® from Berlex Laboratories Inc. The nanoparticles are of sufficient size in order for them to freely egress out of the eye through the trabecular meshwork when the extraocular magnet is removed. The nanoparticles are then cleared by the liver like other iron-based nanoparticles currently used clinically.

The biocompatible material for the biocompatible shell of the magnetic nanoparticles can be selected from the group consisting of polyvinyl alcohol, sodium polyacrylate, acrylate polymers, hyaluronase polymers, collagen membrane, Porous HA/TCP ceramic composite, hydroxyapatite bone cement, PVP/PMMA, tricalcium phosphate, hydroxyapatite coated collagen fibers, calcium sulphate, hydroxyapatite (HAp), phosphorylcholine (PC), silicone, ultrahigh molecular weight polyethylene, polyethylene, acrylic, nylon, Polyurethane, Polypropylene, poly(methyl methacrylate), Teflon, Dacron, acetal, polyester, silicone-collagen composite, polyaldehyde, polyvinyl chloride), silicone-acrylate, poly(tetrafluoroethylene), hydroxyethyl methacrylate (HEMA), poly(methyl methacrylate) (PMMA), poly(glycolide lactide), poly(glycolic acid), tetrafluoroethylene, hexafluoropropylene, poly(glycolic acid), poly(lactic acid), desaminotyrosyltyrosine ethyl ester, polydioxanone, fibrin, gelatin, hyaluronan, tricalcium phosphate, polyglycolide (PGA), polycaprolactone, poly (lactide-co-glycolide), polyhydroxybutyrate, polyhydroxyvalerate, trimethylene carbonate, polyanhydrides, polyorthoesters, poly(vinyl alcohol), poly (N-vinyl 2-pyrrolidone), poly(ethylene glycol), poly(hydroxyethylmethacrylate), n-vinyl-2-pyrrolidone, methacrylic acid, methyl methacrylate, and maleic anhydride, polycaprolactone, poly(amino acids), poly(L-lysine), poly (1-ornithine), poly(glutamic acid), polycyanoacrylates, polyphosphazenes, poly(lactic acid), poly(glycolic acid), crown ethers, cyclodextrins, cyclophanes, ethylene glycol, Methylacrylate, Para-xylylene, Biodegradable Copolymers, Copolymer Surface Coatings, Starch Polymers, Polylactic Acid, Cellophane, Tyrosine Polycarbonates Lactide and Glycolide Polymers, Collagen, PTFE, silicone, Keratin-Based Materials, Fibrous Composites—Carbon Fiber and Particles, Polymer Composites, Artificial/Natural Material Composites, Glass-Ceramic/Metal Composites, Glass-Ceramic/Nonmetal Composites, Dental Composites, hydrogels, timed-release foams, and polymeric carriers.

According to certain implementations, the magnetic nanoparticles can include metal oxide and polymeric or liposomal formulations. Example liposomes include elements from the group consisting of fatty acids, fatty acids derivatives, mono-, di and triglycerides, phospholipids, sphingolipids, cholesterol and steroid derivatives, oils, vitamins and terpenes including but not limited to egg yolk L-phosphatidylcholine (EPC), 1,2-dimyristoyl-sn-glycero-3-phosphatidylcholine (DMPC), 1,2-dipalmitoyl-sn-glycero-3-phosphatidylcholine (DPPC), 1,2-dioleoyl-sn-glycero-3-phosphatidylcholine (DOPC), 1,2-distearoyl-sn-glycero-3-phosphatidylcholine (DSPC), 1,2-dilauroyl-sn-glycero-3-phosphatidylcholine (DLPC), 1,2-dioleoyl-sn-glycero-3-phosphaethanolamine (DOPE), 1-palmitoyl-oleoyl-sn-glycero-3-phosphoethanolamine (POPE), 1,2-dimyristoyl-sn-glycero-3-phosphoethanolamine (DMPE), 1,2-dipalmitoyl-sn-glycero-3-phosphoethanolamine (DPPE), and 1,2-distearoyl-sn-glycero-3-phospharthanolamine (DSPE), phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, 13-acyl-y-alkyl phospholipids, di-oleoyl phosphatidylcholine, di-myristoyl phosphatidylcholine, di-pentadecanoyl phosphatidylcholine, di-lauroyl phosphatidylcholine, dipalmitoylphosphatidylcholine, distearoylphosphatidylcholine, diarachidoylphosphatidylcholine, dibehenoylphosphatidylcholine, ditricosanoylphosphatidylcholine, diligno-ceroylphatidylcholine; and phosphatidylethanolamines.

The polymer formulations (e.g., forming a matrix for the nanoparticles) can be selected from the group consisting of poly(acrylamide), poly(N-isopropylacrylamide), polyiso-propylacrylamide-co-1-vinylimidazole), poly(N,N-dim-ethylacrylamide), poly(N,N-dimethylacrylamide), poly(1-vinylimidazole), poly(sodium acrylate), poly(sodium methacrylate), poly(2-hydroxyethylmethacrylate) (HEMA), poly N-dimethylaminoethyl methacrylate) (DMAEMA), poly(N tris(hydroxymethyl)methylacrylamide), poly(1-(3-methacryloxy)propylsulfonic acid) (sodium salt), poly(al-lylamine), poly(N-acryloxysuccinimide), poly(N-vinyl-caprolactam), poly(1-vinyl-2-pyrrolidone), poly(2-acrylamido-2-methyl-1-propanesulfonic acid) (sodium salt), poly((3-acrylamidopropyl) trimethylammonium chloride), and poly(diallyldimethylammonium chloride), poly(hy-droxy acids), polyanhydrides, polyorthoesters, polyamides, polycarbonates, polyalkylenes, polyalkylene glycols, poly-alkylene oxides, polyalkylene terepthalates, polyvinyl alco-hols, polyvinyl ethers, polyvinyl esters, polyvinyl halides, polyvinylpyrrolidone, polysiloxanes, poly(vinyl alcohols), poly(vinyl acetate), polystyrene, polyurethanes and co-poly-mers thereof, synthetic celluloses, polyacrylic acids, poly (butyric acid), poly(valeric acid), and poly(lactide-co-capro-lactone), ethylene vinyl acetate, copolymers and blends thereof.

Advantageously, the described intraocular base enables customization and exchange of optics as well as delivery of therapeutics.

Magnetic Tack, Screw, and Scleral Buckle

Indwelling affixation magnets, in the form of magnetic tacks, screws, or scleral buckles with fastened magnets, can be used for allowing repeatable coupling and affixation of structures or therapeutic drugs inside non-confined locations within a body.

For example, a magnet embedded in the posterior sclera of an eye can enable one to have magnet tamponade ele-ments that treat retinal detachments. The retina can be held in an appropriate location by having a magnet in the sclera and a magnetic element inside of the eye that sandwiches the retina to the wall of the eye through the magnetic force through the sclera. Another use is to ensure a toric contact lens, which corrects for astigmatism, is held in one orien-tation. This may obviate the need for a ballast on the lens, which has the side effect of swinging.

Alternatively a magnetic fixation element can be placed in the canalicular space. If it is placed proximal in the punctum, then magnetic nanoparticles can be held adjacent to the punctum. If instead the magnet is advanced deeper in the canalicular system until adjacent to the nares, one can attach a magnetic therapeutic element inside the wall of the nose.

In different strategies, a magnetic fixation element can be delivered perilimbally inferiorly. This may be an ideal location to take advantage of gravity as well as magnetic attraction to hold a magnetic hydrogel, polymer, or other depot drug delivery element or therapeutic cell into an appropriate location.

In addition to magnetic polymers, cells can be made to be magnetic through loading cells with magnetic nanoparticles or attaching magnetic nanoparticles to cells through anti-body attraction or other means. Such a magnetic fixation element could enable remote delivery of a therapeutic, for example anywhere in the anterior chamber of the eye, that would then move to the magnetic fixation element and affix in the necessary location.

A similar strategy could be utilized for depot delivery to the sulcus space. A magnetic depot implant can be injected without direct visualization behind the iris. The magnetic element would then move to the magnetic fixation element and stay in the precise location. In the case of a DURYSTA® bimatoprost intracameral implant, manufactured by AbbVie of North Chicago, Illinois, this not only could ensure that the drug delivery polymer is localized adjacent to its main point of target, the ciliary body, but also precludes it from migrat-ing to the vitreous where it is known to have no appreciable intraocular pressure lowering ability.

Firmly and lastingly anchoring magnets to the eye may enable many of the uses described above as well as others.

A "tack" includes a small implantable device used to hold tissue or structures in place within a body, or as otherwise known in the art. Conventional medical tacks are used in vascular and cardiac surgeries, such as angioplasty and stent placement. Such tacks are typically made of materials such as stainless steel, titanium, or bioabsorbable polymers.

Figure 16:
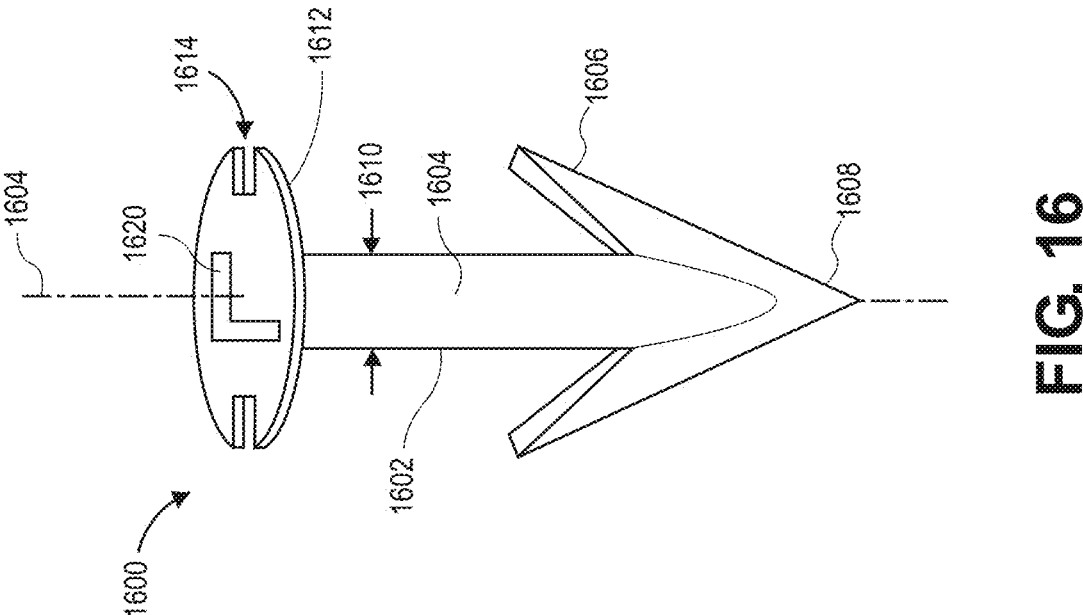
FIG. 16 illustrates a magnetic tack having external notches in accordance with an embodiment.

FIG. 16 illustrates a magnetic soft tissue tack having external notches. System 1600 includes tack 1602 having shaft 1610.

"Soft tissue" includes all biological tissue in an animal or human body that is not hardened by ossification or calcifi-cation such as bones and teeth tissues, or as otherwise known in the art. Soft tissues are resilient and can be somewhat fragile. For example, the sclera of an eye is soft tissue.

Shaft 1610 has diameter 1610, which is less than 2 millimeters (mm). Shaft 1610 has longitudinal axis 1604, which may or may not be defined by physical features at the line. When mounted at its intended point on or within soft biological tissue, axis 1604 is normal to the surface of the tissue.

Shafts can be less than 10 millimeters (mm), 9 mm, 8 mm, 7 mm, 6 mm, 5 mm, 4 mm, 3.5 mm, 3 mm, 2.5 mm, 2 mm, 1.5 mm, 1 mm, 0.75 mm, 0.50 mm, or 0.25 mm in diameter. Their size may be commensurate with the bodily organ that they are targeted to be embedded into.

At the end of shaft 1610 is point 1608, and alongside are barbs 1606. Point 1608 and barbs 1606 are configured to pierce and embed in soft tissue.

On top of shaft 1610 is head 1612. Head 1620 has outer notches 1614 cut in either side to facilitate retention by a surgical tool until point 1608 and barbs 1606 are embedded in tissue. In screw embodiments (described infra), notches can be used to transfer torque from the tool to the shaft and screw threads.

Head 1620 includes fiducial 1620. Besides or in addition to a printed or stamped marking, the fiducial can be made of a material that emits fluorescence or is bioluminescent.

A "fiducial" serves as a reference point or marker that helps establish a spatial relationship or frame of reference. Fiducials are commonly used in a range of scientific, engi-neering, and medical applications for localization, tracking, alignment, and calibration purposes.

Multiple fiducials, affixed to multiple tacks situated around the eye, provide secure, fixed, readily discernable location points on the eye. These points can be directly imaged, x-rayed, or subjected to tomography in order to determine their absolute or relative positions to one another. For example, images may be graphically processed in order to estimate a local surface topology. The positions and topology can be used to determine the precise curvature of the eye and lens position—suitable for ray tracing tech-niques to produce corrective optics. By employing topog-raphy/tomography and wavefront/ray traced measurements of the eye, all the optical variables can be measured and modeled in order to design a custom optic. A corrective optic may be precisely manufactured in vitro and then implanted, magnetically affixed to the tacks or otherwise.

An issue with light adjustable lenses is that their haptics are used to determine the lens center. However, the haptics dynamically move, and they require broad dilation for visualization. By substituting external fiducials and acquiring a 3D map of the eye, such as with the ArcScan Insight 100® ophthalmic ultrasound system manufactured by ArcScan of Golden Colorado, USA, lens center can be determined without visualization of haptics by overlaying imaging.

Shaft 1604 is made of permanent magnetic material that is surrounded by a protective coating of biocompatible polymer, thereby making the shaft biocompatible. The magnetic material serves to attract ferromagnetic metal or other magnets in order to bind them in place within a body. The north-south polarity of the magnet may be aligned with axis 1604 or not aligned to it.

Figure 17:
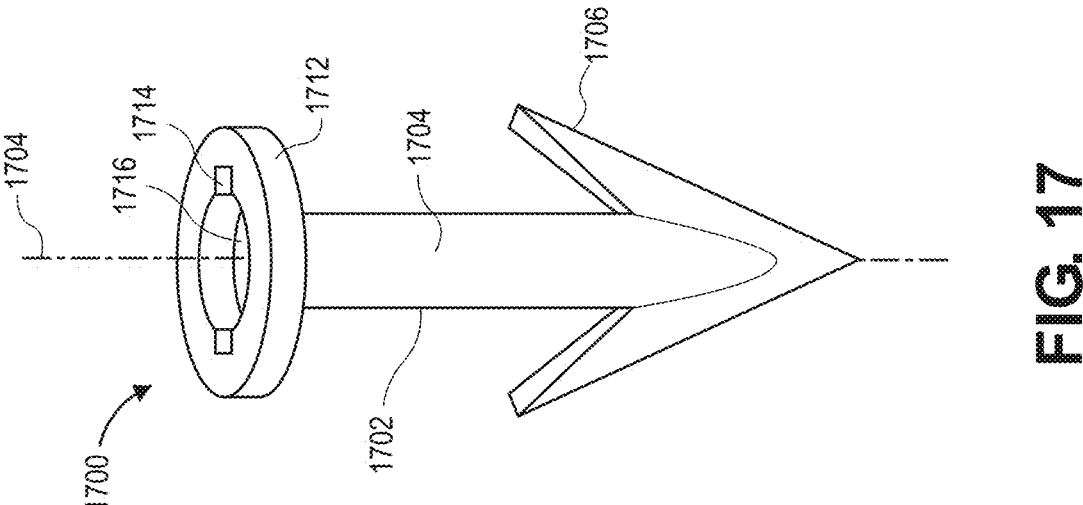
FIG. 17 illustrates a magnetic tack having an internal notch in accordance with an embodiment.

FIG. 17 illustrates a magnetic tack system 1700 that has an internal notch for retention and driving.

Magnetic tack 1702 includes shaft body 1704 that is made of permanently magnetic material. The shaft body is rendered biocompatible by a film of biocompatible polymer. Like the previously described embodiment, tack 1702 has longitudinal axis 1704 and includes barb 1706 for piercing and embedding in soft tissue.

The top portion of shaft 1704 supports wide head 1712. Within head 1712 is recess 1716, which includes a channel and internal notches 1714. The internal notches allow the tack to be held and driven into tissue without sharp edges at its circumference. In embodiments with screw threads, the channel and notches can be used to transfer torque from a tool to the shaft and wind screw threads into the tissue.

Internal notches allow the outside surface of the tack to be smooth, minimizing conjunctival erosion. "Conjunctival erosion" refers to the loss or damage of conjunctival tissue, which is the thin, transparent membrane that covers the white part of the eye (sclera) and lines the inside of the eyelids. Conjunctival erosion can result from various causes, including trauma, infection, inflammation, or underlying medical conditions. This condition can be painful and may lead to discomfort, redness, tearing, and foreign body sensation in the eye.

Alternatives to a push in barb/tack are envisioned.

A "tissue screw" is a medical device used in surgery or orthopedics, used in procedures such as ligament reconstruction or tendon repair to secure soft tissues to bone or to stabilize fractures. Such screws are designed to provide strong fixation while minimizing damage to surrounding tissue. They come in various sizes and designs depending on the specific application and the type of tissue being addressed.

Figure 18:
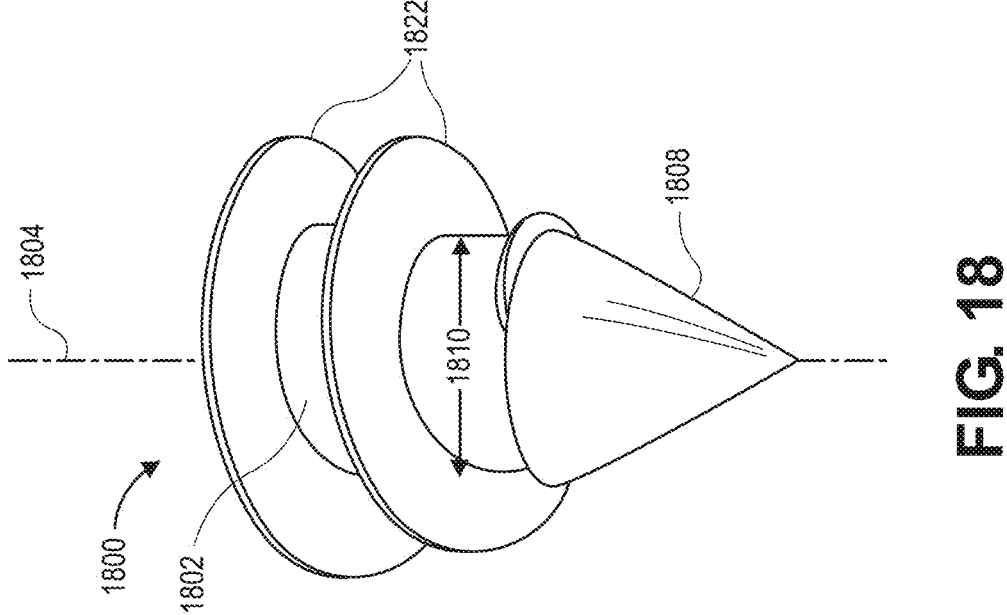
FIG. 18 illustrates a magnetic screw having a straight shank in accordance with an embodiment.

FIG. 18 illustrates a magnetic tissue screw device 1800 having a straight shank.

In orthopedic surgery, tissue screws are made of materials like titanium or stainless steel, which are biocompatible and provide sufficient strength for the intended purpose. Additionally, some tissue screws feature specialized designs, such as threads optimized for gripping bone or smooth shafts to reduce tissue irritation.

Magnetic screw 1802 includes a shaft, or shank, with diameter 1810 and terminating at point 1808. Point 1808 and screw threads 1822 are configured to pierce and embed into tissue, such as the sclera of an eye. When screwed into a sclera, axis 1804 of the shank is configured to be normal to the sclera's local surface. A fiducial (not shown in the view) is on the top surface of the shaft.

The entire shank, screw heads, and point are made of magnetic material and rendered biocompatible with a polymeric coating.

Figure 19:
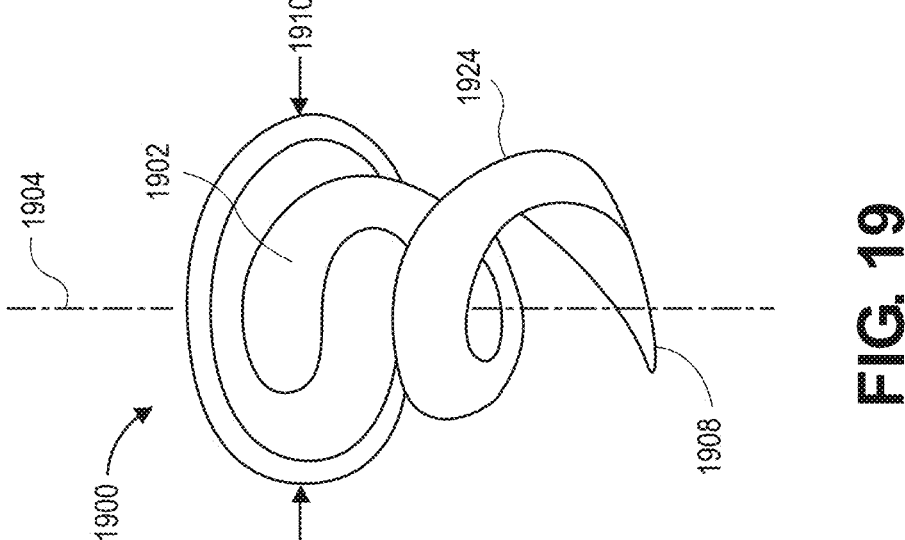
FIG. 19 illustrates a magnetic screw having a helical corkscrew in accordance with an embodiment.

FIG. 19 illustrates a magnetic screw device 1900 having a helical corkscrew to embed within tissue.

Shaft with diameter 1910 comprises a stubby region at the top of screw 1902 and has axis 1904 that is intended to be normal to a surface in which it is embedded. A tapering helical corkscrew 1924 terminates in sharp tip 1908. Like the previously described embodiment, the shaft, corkscrew, and point are made of magnetic material that has been rendered biocompatible.

An advantage of the corkscrew configuration is that a smaller puncture may be needed to drive it into tissue for the same holding power, although they may not be as much magnetic material farther in toward the tip.

Figure 20:
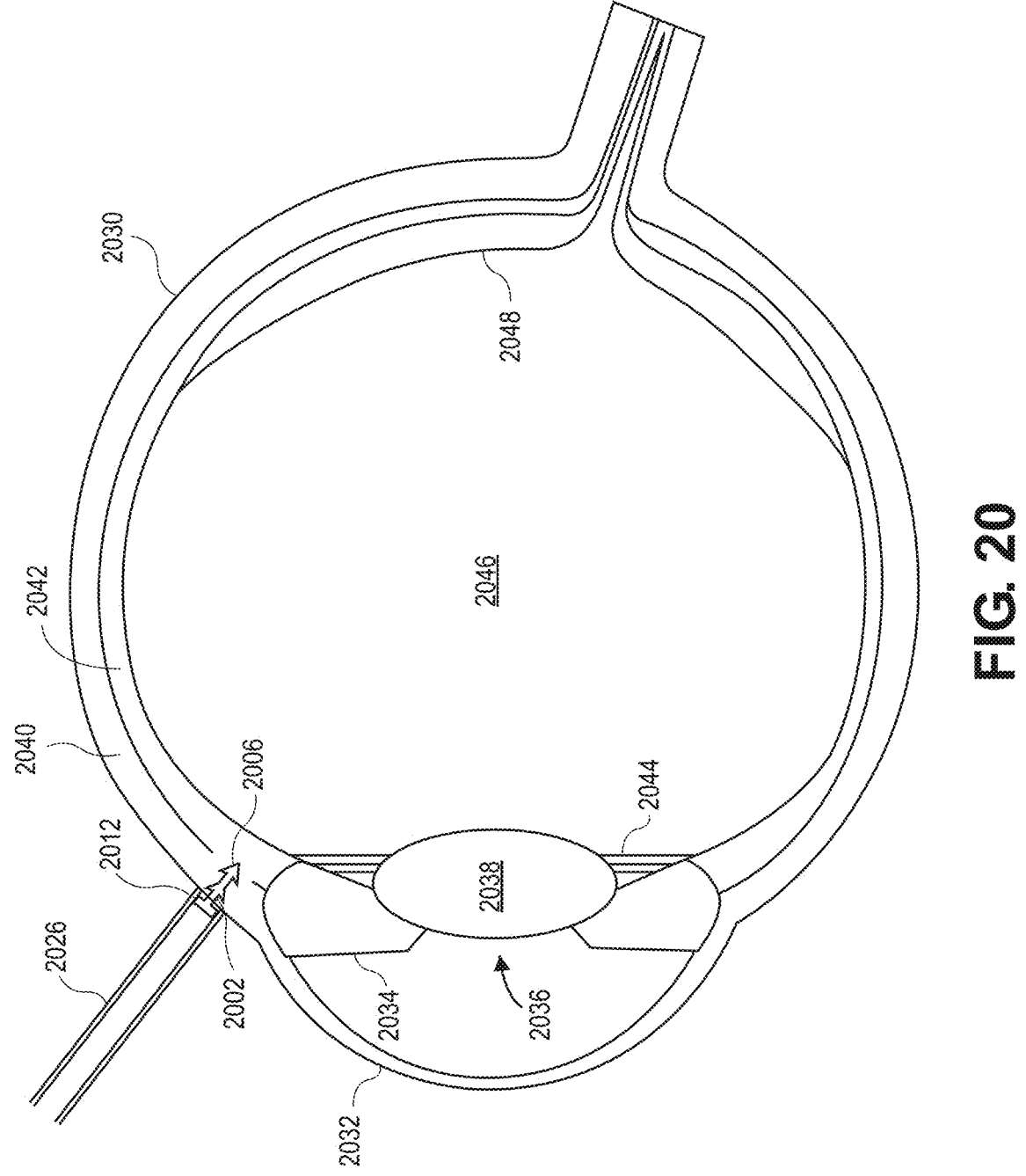
FIG. 20 illustrates insertion of a magnetic tack on the outside of an eye in accordance with an embodiment.

FIG. 20 illustrates insertion of a magnetic tack on the outside of an eye, into the sclera.

At the front of eye 2030 is cornea 2032, which protects iris 2034 and pupil 2036. Pupil 2036 describes the hole within the iris that exposes lens 2038. Lens 2038 is suspended in place by suspensory ligaments of ciliary body 2044. Visible light progresses through cornea 2032, through pupil 2036, and is focused by lens 2038 through optically clear vitreous humor 2046 to form an upside-down image on retina 2048. Most of these structures are quite soft and delicate.

Sclera 2040, which is the outer white portion of an eyeball and underlaid by choroid 2042, is generally soft but forms one of the more rigid structures in the eye compared to others. It is within or on the sclera that permanent magnets may be set.

To fasten a magnet to the eye, an ophthalmologist positions tiny cannula 2026 against sclera 2040. Inside cannula 2026 is magnetic tack 2002. Tack 2002 is pushed out of cannula 2026 such that its point and barb 2006 pierces and embeds itself into sclera 2040. Meanwhile, head 2012 of tack 2002 remains outside of the eye, flush or slightly proud of the outer surface of sclera 2040. Portions of the tack, or the entire tack, are magnetic in order to act as an anchor for later assemblies within the eye.

Figure 21A:
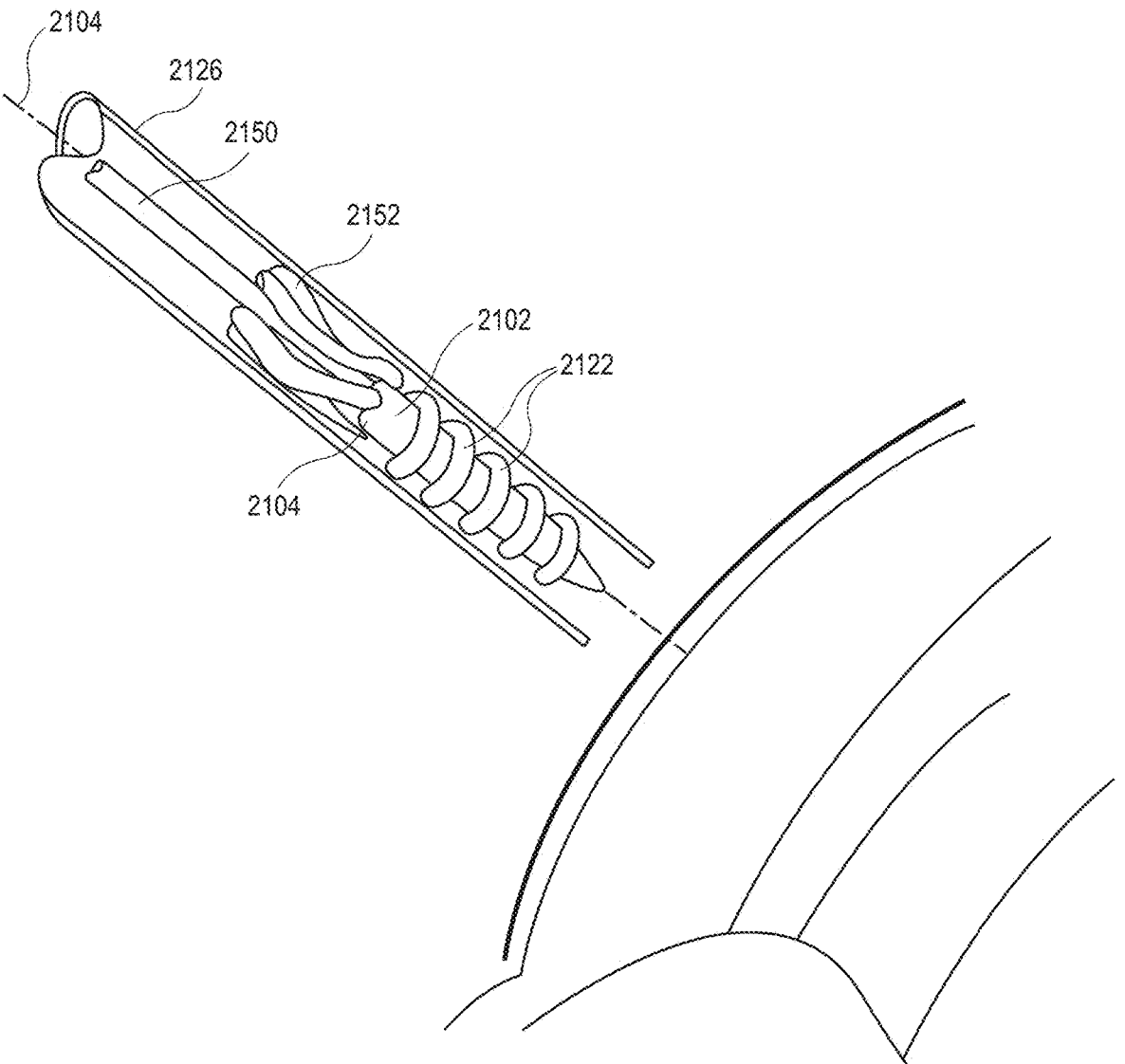
FIG. 21A illustrates a magnetic screw with a deployable flange that is stowed within a cannula in accordance with an embodiment.

FIG. 21A illustrates magnetic screw with a deployable flange that is stowed within a cannula. Within cannula 2126 is magnetic screw 2102 having sharp screw threads 2122.

Deployable flange 2152 is attached around shaft 2104 of magnetic screw 2102. In the figures, flange 2152 is shown in a linear stowed configuration, wrapped upward around axis 2104 and squeezed into a cylinder shape formed by the inner wall of cannula 2126.

Another suitable configuration is for the flange's flexible material to be twisted around the axis in a more confined longitudinal place, such as to form a shorter, squatter cylindrical shape. Still another configuration is to wrap the flange's material downward around the screw threads or tack barb.

Along axis 2104 runs screwdriver shaft 2150, which extends longitudinally through cannula 2126 to the head of magnetic screw 2102. At the distal end of screwdriver shaft 2150 is screwdriver tip 2151 (see FIG. 21B). Flange 2152 wraps around screwdriver shaft 2150 and axis 2104.

This compact configuration allows an ophthalmologist to precisely pinpoint a location on the eye in which to implant the screw without visual obstruction by portions of the tool or screw.

Figure 21B:
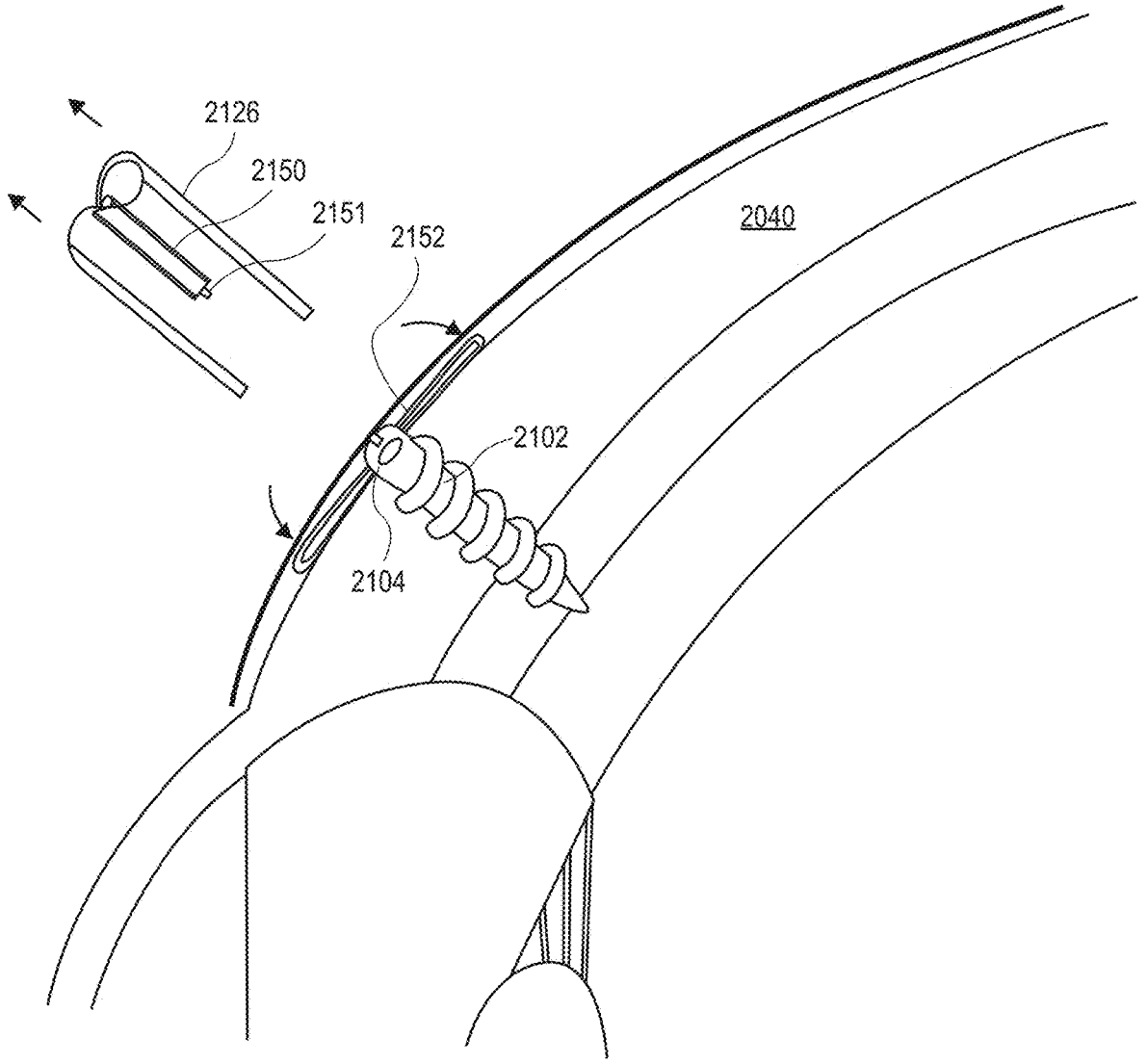
FIG. 21B illustrates the magnetic screw of FIG. 21A with its flange deployed.

FIG. 21B illustrates magnetic screw 2102 after it has been twisted and set into the sclera. Cannula 2126, with screwdriver shaft 2150 and tip 2151 are pulled away from the site, leaving the magnetic screw to reconfigure to a deployed configuration.

Flange 2152, still attached around shaft 2104 of magnetic screw 2102, pivots its petals downward against sclera 2040. Upon pivoting, the petals, and thus the flange, expand outward to circle the shaft 2104 in a plane perpendicular to its longitudinal axis. The flange forms footplates for the screw. The petals broaden the surface area presented to the sclera, lowering stress and strain forces.

In order to move automatically, the flange may be made of a superelastic or shape memory material that is configured to move the flange from the linear stowed configuration to the deployed configuration when it is released from an enclosure. The material can be formed into flower-like petal shapes with numerous loops. These can be scrunched to load linearly into a cannula sheath and then pop open when released from the cannula.

A shorter, squatter packing of the flange can be made to spiral open radially like a twisted propeller that straightens its props. This may allow for better unfurling within a confined, potential space within the conjunctiva. In configurations where the flange is packed downward over the screw threads, the ends of the flange arms may rise up underneath the conjunctiva either independently of or with the action of turning the screw threads into tissue. Similarly, in configurations where the flange is packed downward over one or more tack barbs, the flange arms may rise up to set perpendicularly as the tack point is advanced into tissue, or the flange arms may rise up independently.

A "superelastic" material is one that can undergo a large deformation and recover its original shape upon unloading without permanent deformation, or as otherwise known in the art.

"Shape memory materials" can include metals such as shape memory alloys (SMAs), which are a class of metals that have the ability to "remember" their original shape and return to it when subjected to certain stimuli, typically changes in temperature or stress. SMAs are typically composed of one or more metals, with nickel-titanium (NiTi or Nitinol) being the most common alloy. Other alloys include copper-aluminum-nickel, iron-platinum, and iron-manganese-silicon.

In other embodiments, the petals are engaged like an umbrella with a push rod mechanically pushing each petal into the deployed configuration.

Figure 22:
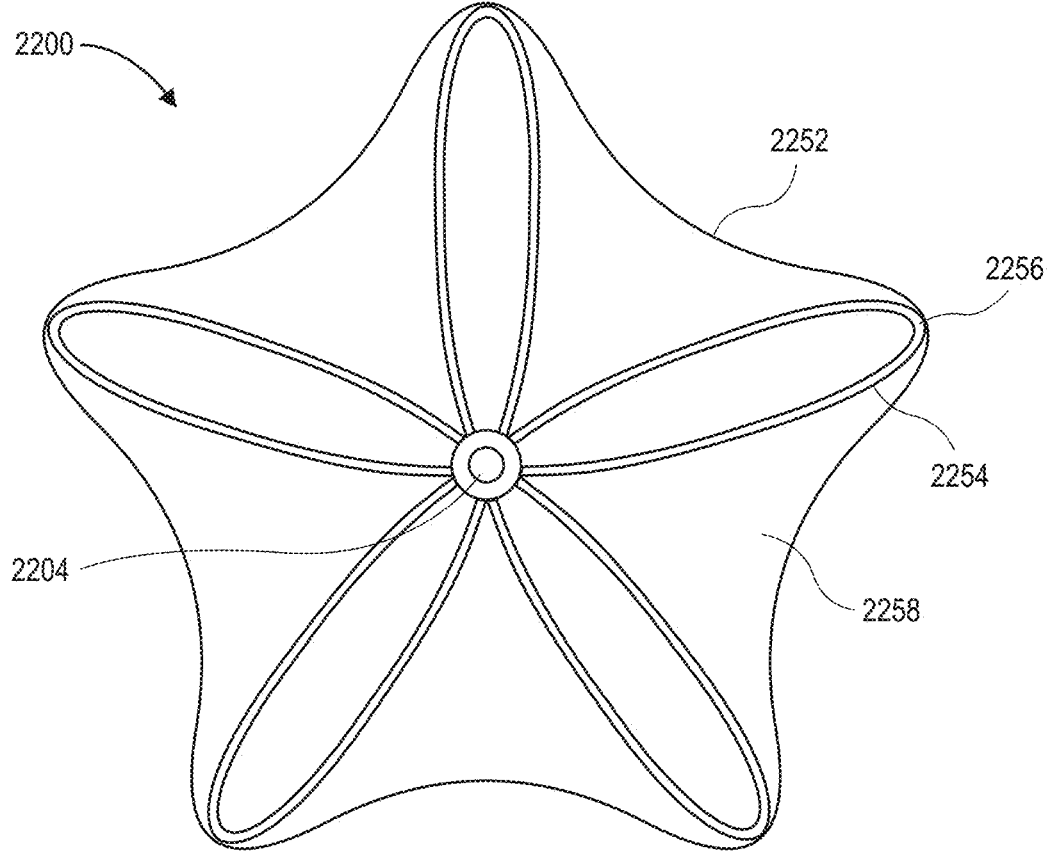
FIG. 22 is a top view of a deployed flange having a polymer sheet over a wire skeleton in accordance with an embodiment.

FIG. 22 is a top view of deployed flange 2252 having a polymer sheet over a wire skeleton. In assembly 2200, five petal loops 2256 surround central shaft 2204. Wire skeleton 2256 has all continuous loops with no sharp wire ends presented to the outside. In some embodiments, more pointed spokes may be used.

Continuous polymer sheet 2258 forms webs between five petals 2256. This helps disperse forces over a broad area of the sclera.

In some embodiments, the petals can be formed of bare nitinol wire. Or metal wire can be covered with a resilient polymer such as polytetrafluoroethylene (PTFE), which helps with biocompatibility and minimizes sharp edges.

In some embodiments, the petal arms may come to a point at their ends and turn downward in a phage-like system. Instead of wrapping around the screwdriver shaft, they can wrap around in a downward triangle.

The petals can have fiducial elements in the membrane, in the screw, the arms, or a combination of these elements. Other configurations of barbs and anchors, and methods of installing, are envisioned.

FIGS. 23A-23F illustrate a hinged magnetic anchor that makes a closed shape for fastening.

FIG. 23A illustrates the insertion of magnetic barb 2306 of hinged anchor 2302 into soft tissue. Just the barb end of hinged anchor protrudes from distal end of cannula 2326. The anchor is forced out of the cannula by a surgeon upon finding a suitable spot for placement. Once the barb is set into the tissue, the rest of hinged anchor 2302 may be deployed.

FIG. 23B illustrates withdrawal of the cannula past a first hinge of hinged anchor 2302. Shown in the figure is the barb set in tissue at the end of linear section 2360. At the proximal end of linear section 2360 is hinge 2362. Upon hinge 2362 is fiducial 2320.

FIG. 23C illustrates further withdrawal of the cannula past a second hinge of hinged anchor 2302. The first linear section 2360 remains in place, and first hinge 2362 connects with a second linear section 2360 to another hinge 2362. A third linear section 2360 is shown emerging from the cannula. The cannula is then withdrawn to allow the hinges to swing freely.

FIG. 23D illustrates entire hinged anchor 2302 after it has been released from the cannula. Hinged anchor 2302 has a proximal magnetic end 2364. The linear sections of hinged anchor 2302 swing freely, moving magnetic end 2364. Magnetic end 2364 may make its way closer to the hinged anchor's barb, which is magnetic.

FIG. 23E illustrates magnetic end 2364 moving close enough to be noticeably attracted to magnetic barb 2306 of hinged anchor 2302. It may do this on its own or be pushed by a surgeon's tool.

FIG. 23F illustrates magnetic end 2364 seating in tissue near magnetic barb 2306 of hinged anchor 2302. The magnets are oriented in such as way so that the south pole of one is facing the north pole of the other, thereby being attracted to one another. The two magnets effectively lock together the linear sections into a closed shape, triangle 2300.

Triangle 2300, anchored at one point in tissue, can be used to tie sutures or pin larger devices to the soft tissue. Its fiducials offer identifying points for determining position and orientation within the eye structure.

Figure 24:
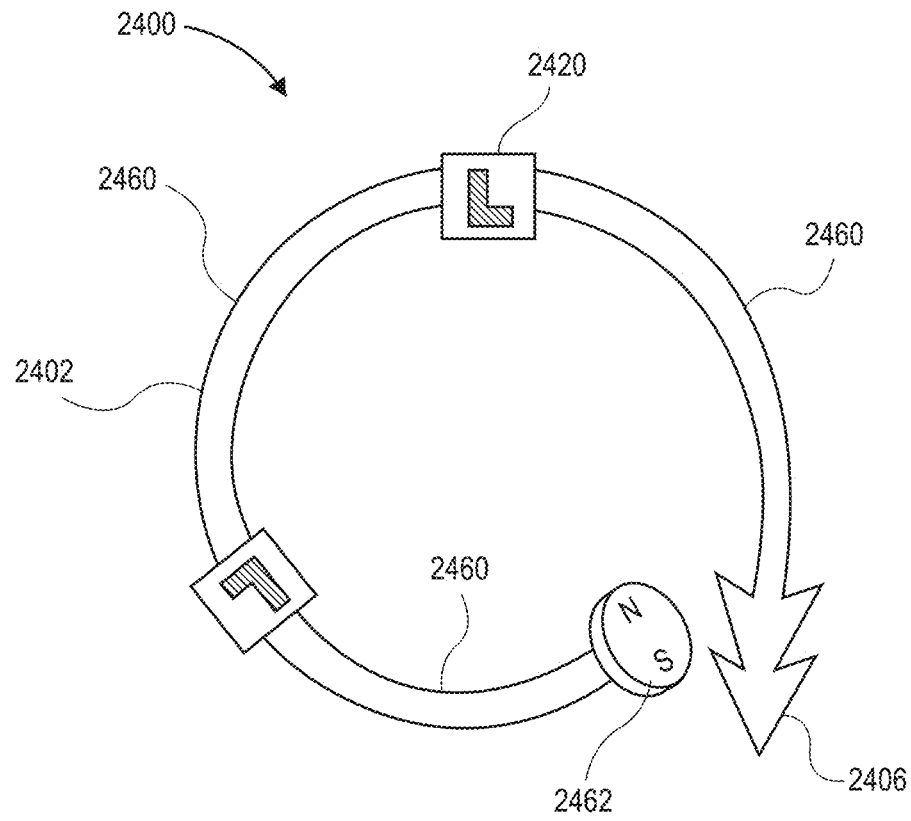
FIG. 24 illustrates a bendable magnetic anchor in accordance with an embodiment.

FIG. 24 illustrates bendable magnetic anchor 2402, which has bendable linear elements instead of straight sections coupled by hinges. Linear elements 2460, separated by non-magnetic fiducials 2420, bend to form a closed shape when magnetic end 2462 is attracted to magnetic barb 2406. The closed shape, loop 2400, can be used to position and anchor other devices.

Figure 25:
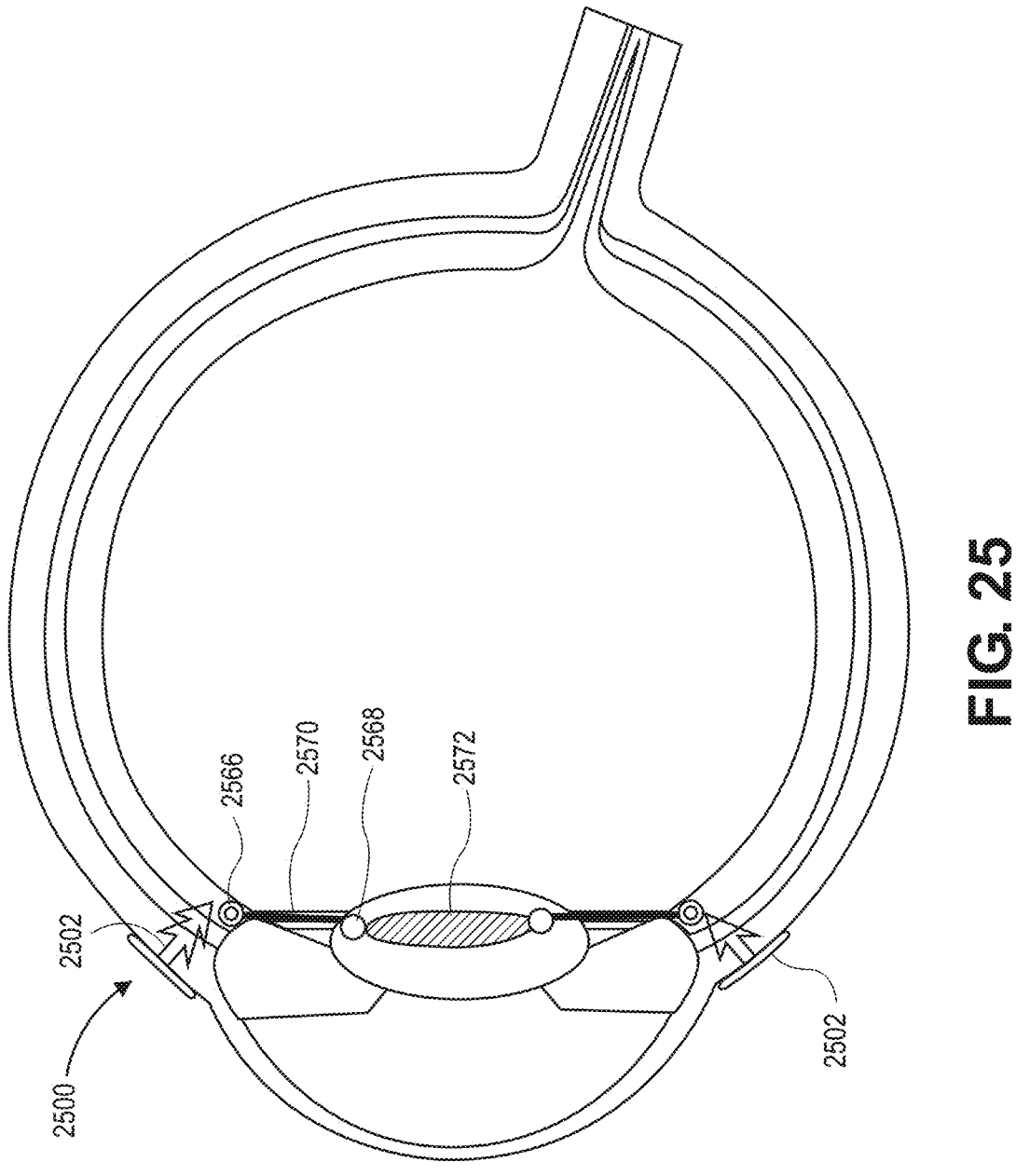
FIG. 25 illustrates suspension of an intraocular lens using anterior intravitreal magnetic fixation points in accordance with an embodiment.

FIG. 25 illustrates optical corrective system 2500 in which there is a suspension of an intraocular lens using anterior intravitreal magnetic fixation points. Magnetic tacks 2502 are anchored into an eye's sclera around the limbus. The tacks, barbs and all, are entirely magnetic so as to attract ferrous metals or other magnets.

Intraocular lens (IOL) 2572 is attached to end 2568 of suspension cable 2570, which is made of flexible wire. An opposite, ring-shaped magnetic end 2566 is magnetically attracted to magnetic tack 2502 and pulled taut. The flexible wire is wrapped through the ring. Another suspension cable is shown anchored below the lens. There may be multiple anchor points that locate the lens at an appropriate position and orientation inside the capsular bag or in other areas inside the eye. The lens may be a wavefront guided/ray traced optic.

Figure 26:
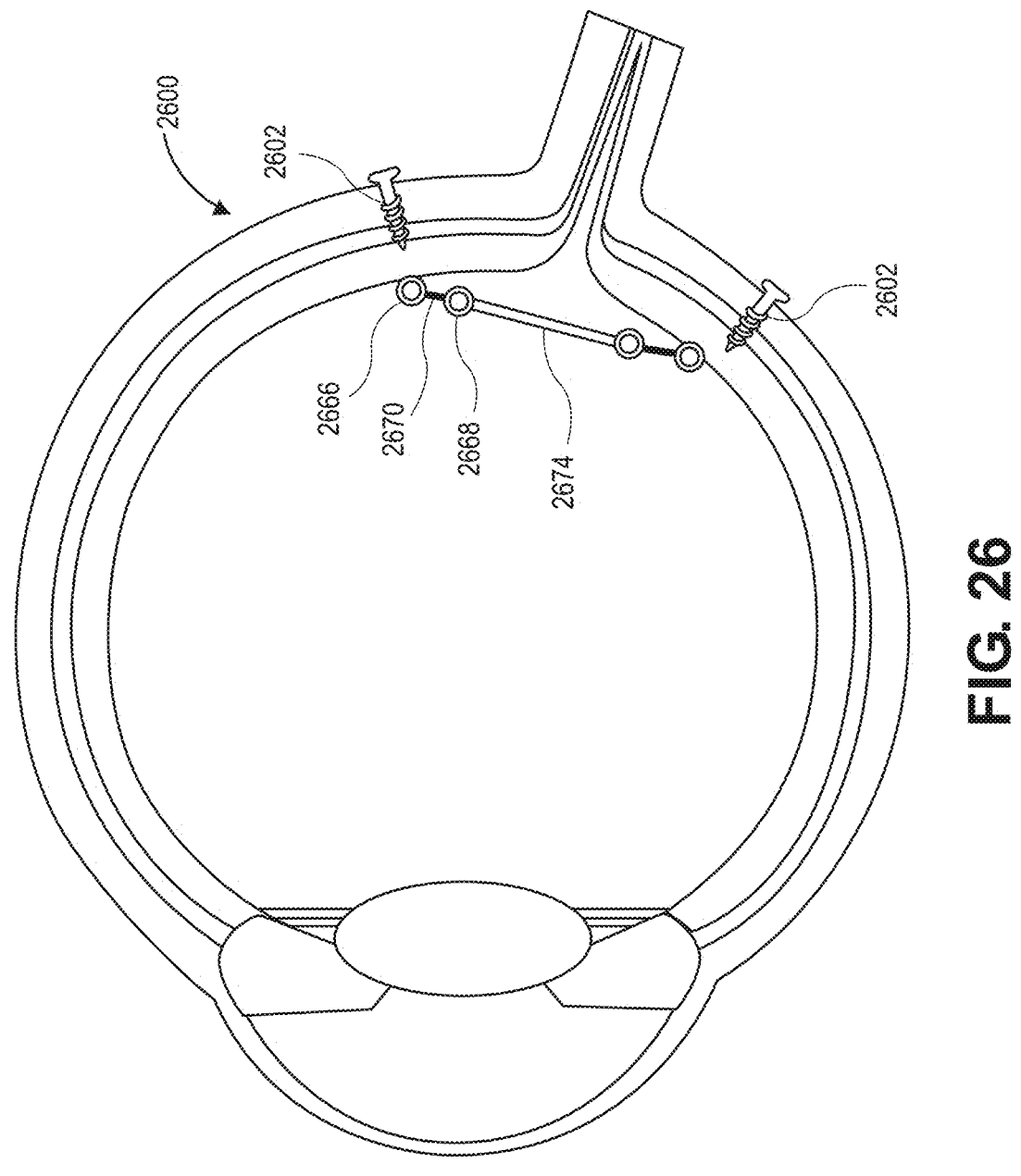
FIG. 26 illustrates suspension of a therapeutic retinal device using posterior intravitreal magnetic fixation points in accordance with an embodiment.

FIG. 26 illustrates retinal therapeutic system 2600 that suspends a therapeutic device over a retina using posterior intravitreal magnetic fixation points. Magnetic screws 2602 are placed at opposite points along the posterior sclera, flanking the retina. Retinal tamponade 2674 is attached to end 2668 of suspension cable 2670. End 2668 may be magnetic or nonmagnetic. The opposite end of suspension cable 2670 terminates at magnetic end 2666.

Magnetic end 2666 is magnetically attracted to magnetic screw 2602 as long as opposite poles are presented to each other. Given the tiny distances between the magnets, the force provided is strong enough to hold them in position.

Retinal therapeutic system 2600 can be suspended or pinned against the retina to help heal the retina from a retinal detachment or promote growth of rehabilitative tissue.

Similarly, magnetic tacks and screws may be applied to the front of the eye in order to affix optical or non-optical elements in place. For example, they can be used with or without suspension cables to therapeutically affix tissue and hold it against an inside wall of the eye between multiple tacks using a tamponade. The tacks themselves may be used to align and pin detached tissue so that it re-grows in place.

Each tack or screw may be left permanently in the eye or removed after a period of time or when corrections are sufficient for them to be no longer required.

Figure 27:
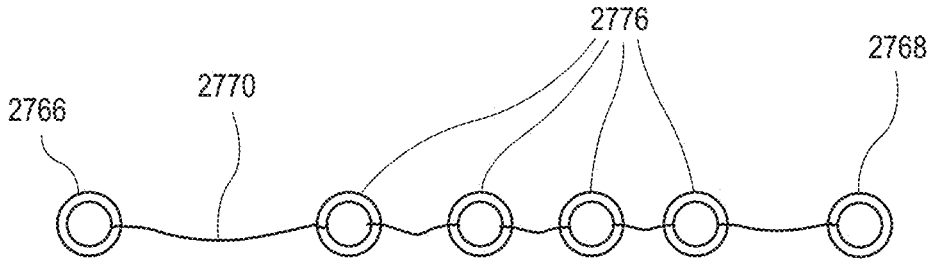
FIG. 27 illustrates a suspension cable having multiple magnets for length adjustments in accordance with an embodiment.

FIG. 27 illustrates suspension cable 2770 having multiple magnets for length adjustments in accordance with an embodiment.

Between suspension cable end 2766 and end 2768 are multiple magnets for shortening. Each shortening magnet 2776 allows the cable to be doubled back over itself. For example, the two rightmost magnets 2776 may be snapped together so that the entire length of suspension cable 2770 is shortened by the length of wire that is between them. The cable may be lengthened and shortened before or during surgery as needed.

Figure 28:
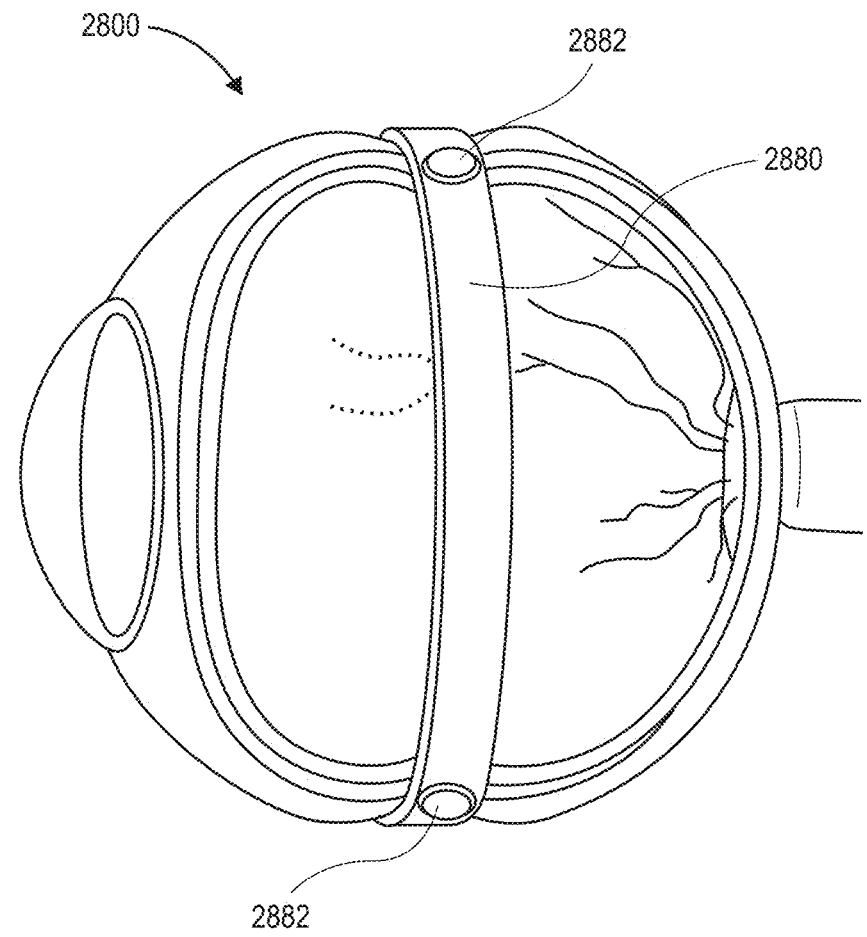
FIG. 28 illustrates a scleral buckle having permanent magnets in accordance with an embodiment.

FIG. 28 illustrates a scleral buckle having permanent magnets, wrapped around an eye in system 2800. Scleral buckling surgery involves placing a silicone band (buckle) around the eye to support the retina and help it reattach properly. Conventional ocular tacks or sutures may be used in conjunction with the buckle to secure the retina in place.

Biocompatible, permanent magnets 2882 are attached to scleral buckle 2880. Magnets 2882 are spaced from each other so as to be symmetrically located around a circumference of the sclera. The can include fiducial shapes, or other fiducial shapes may be attached to the scleral buckle As with other embodiments, there may be 1, 2, 3, 4, 5, 6, 7, 8, 9, 10, or more magnets spaced around the eye so has to provide magnetic fixation points where needed for items within the eye.

Suspension cables, tethers, or other systems may be magnetically captured—on the inside of the eye—to the sclera buckle magnets in order to keep them in position.

Drug Delivery

In addition to the indwelling magnetic anchors affixing structures or other devices as described above, they can also be used to deliver therapeutic drugs. Magnetic nanoparticles may be incorporated into drug formulations, and their capture at particular positions allows for precise control over drug delivery. The drug molecules can be guided to a target site within a body, such as one with a magnetic tack or screw, using an external magnetic field. Once the nanoparticles reach the desired location, the drug is released, resulting in localized and targeted therapy near the magnetic tack or screw.

"Magnetic nanoparticles" includes tiny particles, typically with dimensions ranging from 1 to 100 nanometers, that exhibit magnetic properties, or as otherwise known in the art. These nanoparticles can be composed of magnetic materials such as iron oxide (e.g., magnetite or maghemite), iron, cobalt, nickel, or their alloys. Due to their small size, they often exhibit unique magnetic properties that differ from their bulk counterparts. In addition to, or in place of, incorporating into drug formulations, magnetic particles can be buried in a lens or a base or included in a tack/screw.

In some embodiments, the nanoparticles are selected from the group consisting of cobalt nanoparticles, iron oxide nanopowder, niobium oxide nanopowder, thulium nanoparticles, cobalt oxide nanopowder, lanthanum nanoparticles, palladium nanoparticles, tin nanoparticles, aluminum oxide nanopowder, copper nanoparticles, lanthanum oxide nanopowder, platinum nanoparticles, tin oxide nanopowder, antimony nanoparticles, copper oxide nanopowder, praseodymium nanoparticles, titanium carbide nanoparticles, antimony oxide nanopowder, dysprosium nanoparticles, lithium manganese oxide nanoparticles, praseodymium oxide nanopowder, titanium nanoparticles, antimony tin oxide (ATO) nanoparticles, dysprosium oxide nanopowder, lithium nanoparticles, rhenium nanoparticles, titanium nitride nanoparticles, barium titanate nanoparticles, erbium nanoparticles, lithium titanate nanoparticles, ruthenium nanoparticles, titanium oxide nanopowder, beryllium nanoparticles, erbium oxide nanopowder, lithium vanadate nanoparticles, samarium nanoparticles, tungsten carbide nanoparticles, bismuth oxide nanopowder, europium nanoparticles, lutetium nanoparticles, samarium oxide nanopowder, tungsten nanoparticles, boron carbide nanoparticles, europium oxide nanopowder, magnesium nanoparticles, silicon carbide nanoparticles, tungsten oxide nanopowder, boron nitride nanoparticles, gadolinium nanoparticles, magnesium oxide nanopowder, silicon nanoparticles, vanadium oxide nanopowder, calcium carbonate nanoparticles, gadolinium oxide nanopowder, manganese nanoparticles, silicon nanotubes, ytterbium nanoparticles, calcium chloride nanoparticles, gold nanoparticles, manganese oxide nanopowder, silicon nitride nanoparticles, yttria stabilized zirconia, calcium oxide nanopowder, hafnium oxide nanopowder, molybdenum nanoparticles, silicon oxide nanopowder, yttrium nanoparticles, calcium phosphate nanoparticles, holmium nanoparticles, molybdenum oxide nanopowder, silver nanoparticles, zinc oxide nanopowder, carbon nanohorns, indium nanoparticles, neodymium nanoparticles, strontium carbonate nanoparticles, zirconium nanoparticles, carbon nanoparticles, indium oxide nanopowder, neodymium oxide nanopowder, strontium titanate nanoparticles, zirconium oxide nanopowder, carbon nanotubes, iridium nanoparticles, nickel nanoparticles, tantalum nanoparticles, cerium nanoparticles, iron cobalt nanopowder, nickel oxide nanopowder, tantalum oxide nanopowder, cerium oxide nanopowder, iron nanoparticles, nickel titanium nanopowder, terbium nanoparticles, chromium oxide nanopowder, iron nickel nanopowder, niobium nanoparticles, terbium oxide nanopowder, carbon 60 fullerenes, carbon 70 fullerenes and carbon 85 fullerenes, single wall carbon nanotubes, multi-wall carbon nanotubes, and carbon nanofibers.

In certain embodiments, instead of the magnetic nanoparticle being directly conjugated to a drug, the nanoparticles can be embedded in a polymeric implant such as the DURYSTA® bimatoprost intracameral implant.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:

1. A scleral anchor apparatus sized and configured for anchoring to a sclera of an eye, the apparatus comprising:
   a shaft less than 3 millimeters in diameter and having an axis configured to be normal to a surface of the sclera, the shaft being comprised of a biocompatible permanent magnet;
   scleral-engaging screw threads formed along the shaft and configured to pierce and embed in the sclera; and
   a deployable flange surrounding the shaft, the flange configured to move between a stowed configuration, in which the flange is wrapped around the axis, to a deployed configuration, in which the flange expands outward to surround the shaft.

2. The apparatus of claim 1, further comprising:
   a superelastic material configured to move the flange from the stowed configuration, in which the flange is squeezed into a cylinder around the axis, to the deployed configuration, in which the flange expands outward to surround the shaft.

3. The apparatus of claim 2 wherein the superelastic material includes nitinol wire.

4. The apparatus of claim 1 wherein the flange comprises:
   a wire skeleton having continuous loops and no sharp wire end.

5. The apparatus of claim 4 wherein the flange further comprises:
   a continuous polymer sheet over the wire skeleton.

6. The apparatus of claim 4 wherein the flange further comprises:
   a resilient polymer coating the wire skeleton.

7. The apparatus of claim 1 further comprising:
   a fiducial shape connected with the shaft.

8. An intraocular lens system, the system comprising:
   the scleral anchor apparatus of claim 1;
   an intraocular lens; and
   a suspension cable having an end configured to attach with the intraocular lens and an opposite magnetic end or a metallic end configured to magnetically mate with the permanent magnet.

9. The apparatus of claim 8 wherein the intraocular lens includes a ray traced optic.

10. The apparatus of claim 8 wherein the end configured to attach with the lens includes a magnet.

11. The apparatus of claim 10 wherein the magnetic end includes a ring-shaped magnet through which the cable is wrapped and fastened.

* * * * *